1

United States Patent
Rajamani et al.

(10) Patent No.: US 9,060,713 B2
(45) Date of Patent: Jun. 23, 2015

(54) SENSING TISSUE PROPERTIES

(75) Inventors: Rajesh Rajamani, Saint Paul, MN (US); Peng Peng, Falcon Heights, MN (US); Ahmet Serdar Sezen, Minneapolis, MN (US); Arthur G. Erdman, New Brighton, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 763 days.

(21) Appl. No.: 13/263,411

(22) PCT Filed: Apr. 7, 2010

(86) PCT No.: PCT/US2010/030213
§ 371 (c)(1),
(2), (4) Date: Oct. 7, 2011

(87) PCT Pub. No.: WO2010/118117
PCT Pub. Date: Oct. 14, 2010

(65) Prior Publication Data
US 2012/0041345 A1   Feb. 16, 2012

Related U.S. Application Data

(60) Provisional application No. 61/167,324, filed on Apr. 7, 2009.

(51) Int. Cl.
*A61B 5/103* (2006.01)
*A61B 5/117* (2006.01)
*A61B 5/00* (2006.01)

(52) U.S. Cl.
CPC .............. *A61B 5/103* (2013.01); *A61B 5/4514* (2013.01); *A61B 5/4533* (2013.01); *A61B 2562/028* (2013.01); *A61B 2562/043* (2013.01); *A61B 2562/046* (2013.01); *A61B 2562/12* (2013.01); *A61B 2562/164* (2013.01)

(58) Field of Classification Search
CPC ................................. A61B 5/103; A61B 5/107
USPC .................................................... 600/587–595
See application file for complete search history.

(56) References Cited

U.S. PATENT DOCUMENTS 5,836,894 A    11/1998  Sarvazyan
2005/0043623 A1*  2/2005  Jurvelin et al. ............... 600/449

(Continued)

FOREIGN PATENT DOCUMENTS

WO    WO2009/029627    3/2009

OTHER PUBLICATIONS

European Patent Office, International Search Report and Written Opinion, International application No. PCT/US2010/030213, mailed Jul. 22, 2010 Oct. 2011, 24 pages.

(Continued)

*Primary Examiner* — Max Hindenburg
*Assistant Examiner* — Jonathan M Foreman
(74) *Attorney, Agent, or Firm* — Fish & Richardson P.C.

(57) ABSTRACT

Some embodiments of a tissue sensor may include a microfabricated structure that can be coupled to a medical instrument, such as a probe, an endoscopic tool, or another minimally invasive instrument. The tissue sensor can be configured to provide information indicate of tissue properties, such as tissue elasticity characteristics or the type of tissue.

33 Claims, 17 Drawing Sheets

(56) References Cited

U.S. PATENT DOCUMENTS

2009/0005708 A1  1/2009  Johanson et al.
2009/0216119 A1  8/2009  Fan et al.

OTHER PUBLICATIONS

International Bureau of WIPO, International Preliminary Report on Patentability, International Application No. PCT/US2010/030213, mailed Oct. 20, 2011, 13 pages.

Peng, et tal. "Novel MEMS Stiffness Sensor for in-vivo tissue Characterization" *Engineering in Medicine and Biology Society*, 2009, 31$^{st}$ International Conferene of the IEEE EMBS, Minneapolis MN, Sep. 2-6, 2009, pp. 6640-6643.

Lyyra, et al. "In Vivo Characterization of Indentation Stiffness of Articular Cartilage in the Normal Human Knee," *Journal of Biomedical Materials Research*, vol. 48, 1999, pp. 482-487.

Dargahi, et al., "A micromachined piezoelectric tactile sensor for an endoscopic grasper-theory, fabrication and experiments," *Journal of Microelectromechanical Systems*, IEEE Service Center, vol. 9, No. 3, pp. 329-335, Sep. 2000.

Dargahi, et al., "Modelling and testing of a sensor capable of determining the stiffness of biological tissues," *Canadian Journal of Electrical and Computer Engineering*, vol. 32, No. 1, pp. 45-51, 2007.

Lyyra, et al. "Indentation instrument for the measurement of cartilage stiffness under arthroscopic control," *Medical Engineering & Physics*, vol. 17, No. 5, pp. 395-399, Jul. 1995.

\* cited by examiner

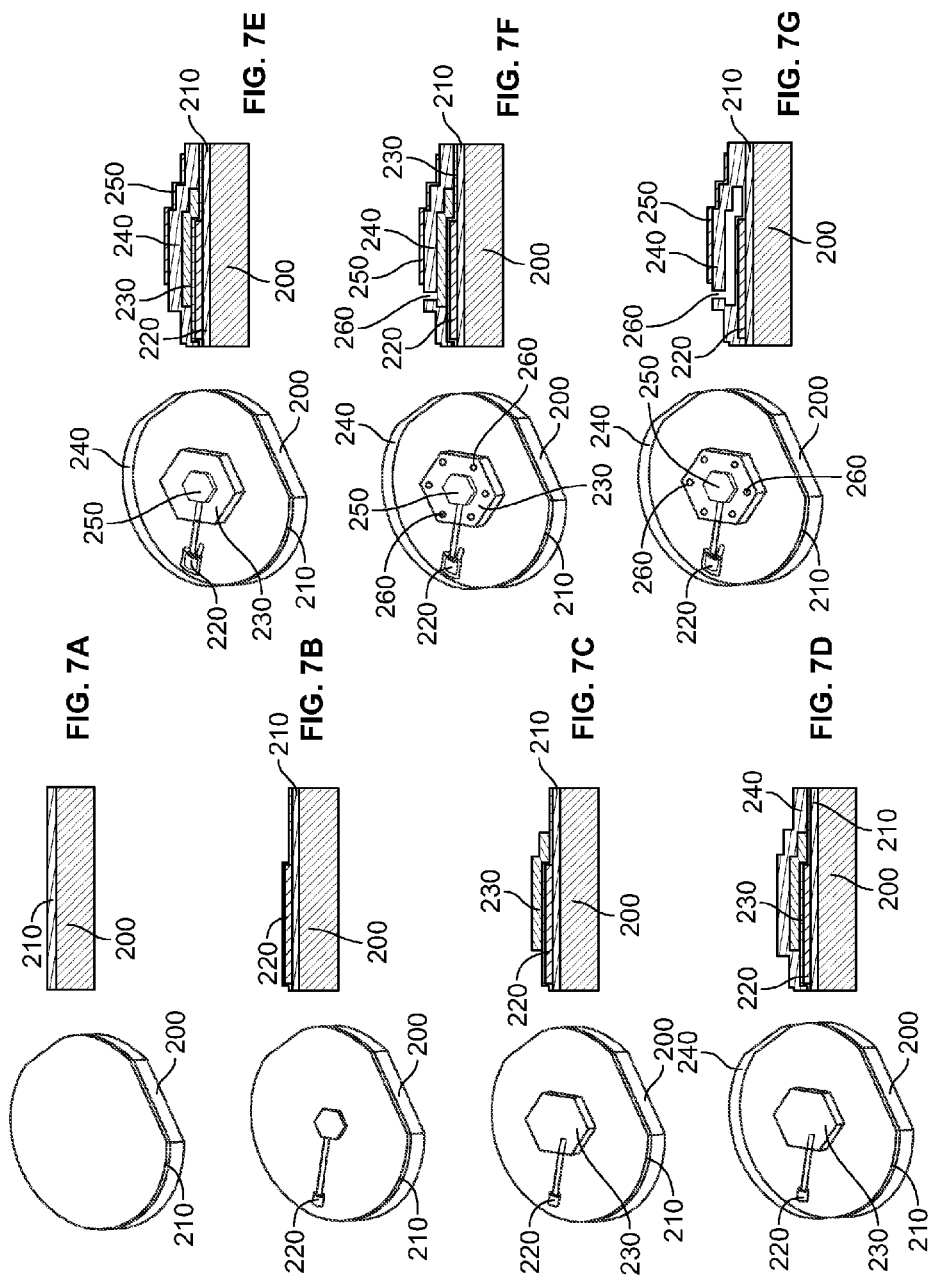

SENSING TISSUE PROPERTIES

GOVERNMENT SUPPORT

The invention described herein was made in part with funding under a grant no. 0652208, from the National Science Foundation. The U.S. government may have certain rights in the claimed subject matter.

CROSS-REFERENCE TO RELATED APPLICATIONS

This application is a National Stage application under 35 U.S.C. 371 and claims benefit under 35 U.S.C. 119(a) of International Application No. PCT/US2010/030213, having an International Filing Date of Apr. 7, 2010, which claims the benefit of U.S. Application Ser. No. 61/167,324 filed on Apr. 7, 2009. The disclosures of the prior applications are considered part of (and are incorporated by reference in) the disclosure of this application

TECHNICAL FIELD

This document relates to sensors that can be coupled to a medical instrument, such as a minimally invasive surgical instrument, so as to provide information indicative of tissue properties, contact force or the like.

BACKGROUND

Information related to tissue elasticity or other properties can be useful to a surgeon or other practitioner during a medical procedure. For example, the elasticity modulus of bodily tissue may indicate the presence of a certain type of tissue. In another example, a measurement of tissue elasticity or stiffness may provide information indicative of tissue damage, disease, or other conditions at a targeted tissue site.

A number of instruments can be used to measure the tissue elasticity of a selected portion of bodily tissue. Many on these instruments measure the resulting force or pressure in response to a predetermined indentation or displacement. Conversely, another group of instruments measure the resulting displacement in response to a predetermined force or pressure. For example, some in vitro measurement devices can receive a tissue sample removed from the body and thereafter apply a predetermined indentation or displacement to the tissue sample. The corresponding force required for making the indentation can be detected, and the elastic modulus or other tissue elasticity properties can then be calculated from force-displacement data.

Some tissue elasticity devices are capable of measuring tissue elasticity in vivo, and thus do not require removal of a tissue sample from a body. For instance, some tissue elasticity measurement devices may include an actuator along an end effector to act upon a targeted tissue site in the body. The actuator may be electrically triggered (e.g., piezoelectric actuator or the like) to apply a controlled dynamic load or otherwise act upon the targeted tissue site, and the response from the targeted tissue can then be detected. In such circumstances, the actuator and other structures on the end effector may require a footprint size that thereby limits the types of surgical procedures suitable for the device.

SUMMARY

Some embodiments of a tissue sensor may include a micro-fabricated structure that can be coupled to a medical instrument, such as a probe, an endoscopic tool, or another minimally invasive instrument. The tissue sensor can be configured to provide information indicate of tissue properties, such as tissue elasticity characteristics or the type of tissue. In particular embodiments, the tissue elasticity sensor can be configured to determine the elasticity of a targeted tissue without requiring a predetermined force or displacement. Accordingly, a surgeon or other user can receive pertinent information indicative of tissue elasticity or type of tissue adjacent to or in contact with the medical instrument during a minimally invasive procedure.

Certain embodiments of a medical system may include a medical instrument having a distal portion insertable into a body and toward a targeted tissue. The system may further include one or more tissue elasticity sensors coupled to the distal portion of the medical instrument. The one or more tissue elasticity sensors may transmit sensor signals in response to application of a force on the targeted tissue in the body that causes a displacement of the targeted tissue. The system may further include a control unit to determine both the Young's modulus of the targeted tissue and the shear modulus of the targeted tissue in the body in response to the sensor signals after the application of the force on the targeted tissue that causes the displacement of the targeted tissue.

In some embodiments, a medical system may include a medical instrument having a distal portion deliverable toward a targeted material. The system may also include one or more material elasticity sensors coupled to the distal portion of the medical instrument. The one or more material elasticity sensors may transmit sensor signals in response to application of an uncontrolled force on the targeted material that causes a non-predetermined displacement of the targeted material. The system may further include a control unit to determine a material elasticity modulus value of the targeted material in response to the sensor signals after the application of the uncontrolled force on the targeted material that causes the uncontrolled displacement of the targeted material. In some aspects, the targeted material may comprise bodily tissue (in a body or a sample removed from a body), and the material elasticity sensors may serve as tissue elasticity sensors for use in the body or external to the body.

In further embodiments, a minimally invasive surgical device may include a working end portion insertable into a body and toward a targeted tissue. The device may also include one or more tissue elasticity sensors mounted to the working end portion. Each tissue elasticity sensor may comprise a micro-fabricated structure including at least two flexible membranes adjacent to two capacitive gaps. The at least two flexible membranes may have different stiffness characteristics from one another. Also, the at least two flexible membranes of each tissue elasticity sensor displace differently in response to application of a contact force between the tissue elasticity sensor and the targeted tissue.

Some embodiments may include an in vivo tissue property sensor for sensing a material property of a targeted tissue in a body. The tissue property sensor may include a flexible substrate attachable to a contoured portion of a medical device. The tissue property sensor may also include a micro-fabricated parallel capacitor array formed on the flexible substrate. The capacitor array may include a first capacitive gap that separates two electrodes and a neighboring capacitive gap that separates two electrodes. The first capacitive gap may have a different size than the neighboring capacitive gap such that the first and second capacitive gaps displace differently in response to application of a contact force upon the micro-fabricated parallel capacitor array.

In further embodiments, a medical system includes a medical instrument having a contoured distal portion insertable into a body and toward a targeted tissue. The system may also include a flexible sensor substrate attached to the contoured distal portion of the medical instrument. The flexible sensor substrate may comprise a micro-fabricated parallel capacitor array including a first capacitive gap that separates two electrodes and a second capacitive gap that separates two electrodes. The first and second capacitive gaps may displace differently in response to application of a tissue contact force applied at an interface of the flexible sensor substrate and the targeted tissue. The system may further include a control unit to display a spatial map of tissue elasticity properties along the interface of the flexible sensor substrate and the targeted tissue in response to sensor signals from micro-fabricated parallel capacitor array.

In other embodiments, a method of evaluating a bodily tissue property may include inserting a distal tip portion of a medical instrument into a body and toward a targeted body tissue. The method may also include contacting one or more tissue elasticity sensors coupled to the distal tip portion of the medical instrument with the targeted body tissue by application of non-predetermined force from the medical instrument on the targeted body tissue to cause a non-predetermined displacement of the targeted body tissue. The method may further include viewing a displayed value of the tissue elasticity modulus value of the targeted body tissue that is generated in the in response to sensor data from the one or more tissue elasticity sensors coupled to the distal tip portion of the medical instrument.

In some embodiments, a method of making a medical instrument may include forming an array of tissue elasticity sensors in a chemical vapor deposition process. Each tissue elasticity sensor may comprise a first capacitive gap that separates two electrodes, a neighboring capacitive gap that separates two electrodes, a first portion of a membrane layer that is adjacent to the first capacitive gap, and a second portion of the membrane layer that is adjacent to the neighboring capacitive gap. The method may also include bonding the array of tissue elasticity sensors to a distal portion of a surgical tool such that the first and second portions of the membrane layer of one of the tissue elasticity sensors displace differently in response to application of a contact force upon the distal tip portion of the surgical tool.

Some or all of the embodiments described herein may provide one or more of the following advantages. First, a surgical tool suitable for use in a minimally invasive procedure can be equipped with a micro-fabricated tissue elasticity sensor to provide real-time feedback indicative of tissue properties, such as an elasticity modulus, a stiffness value, or the like. Second, the tissue elasticity sensors described herein can be employed to measure both normal tissue elasticity (e.g., Young's modulus in some embodiments) and shear tissue elasticity (e.g., shear modulus in some embodiments) at a targeted tissue site. Third, some embodiments of the tissue elasticity sensors can be configured to measure tissue elasticity merely by contacting the tissue, without the use of either a controlled force or a controlled displacement. Fourth, the tissue elasticity sensors described herein may employ capacitive membranes that can be micro-fabricated to a small size for use in a variety of minimally invasive applications. Fifth, the system described herein can output a measurement of the elasticity modulus (e.g., Young's modulus) of the targeted tissue, thereby providing a measurement of the tissue elasticity properties independent of tissue thickness or tissue geometry. Sixth, an array of the sensors can be fabricated as flexible sheets. In such circumstances, the array of sensors can provide a map of elasticity modulus as a function of location. Seventh, in some embodiments, the flexible sheets with the array of sensors can be bonded or otherwise mounted to a contoured tip portion of an instrument. Eighth, the flexible sheets having an array of tissue elasticity sensors can be configured to withstand high shear loads without failure and be mechanically robust.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 7A-G show an exemplary process for fabricating a tissue elasticity sensor.

DETAILED DESCRIPTION OF ILLUSTRATIVE EMBODIMENTS

Figure 1A:
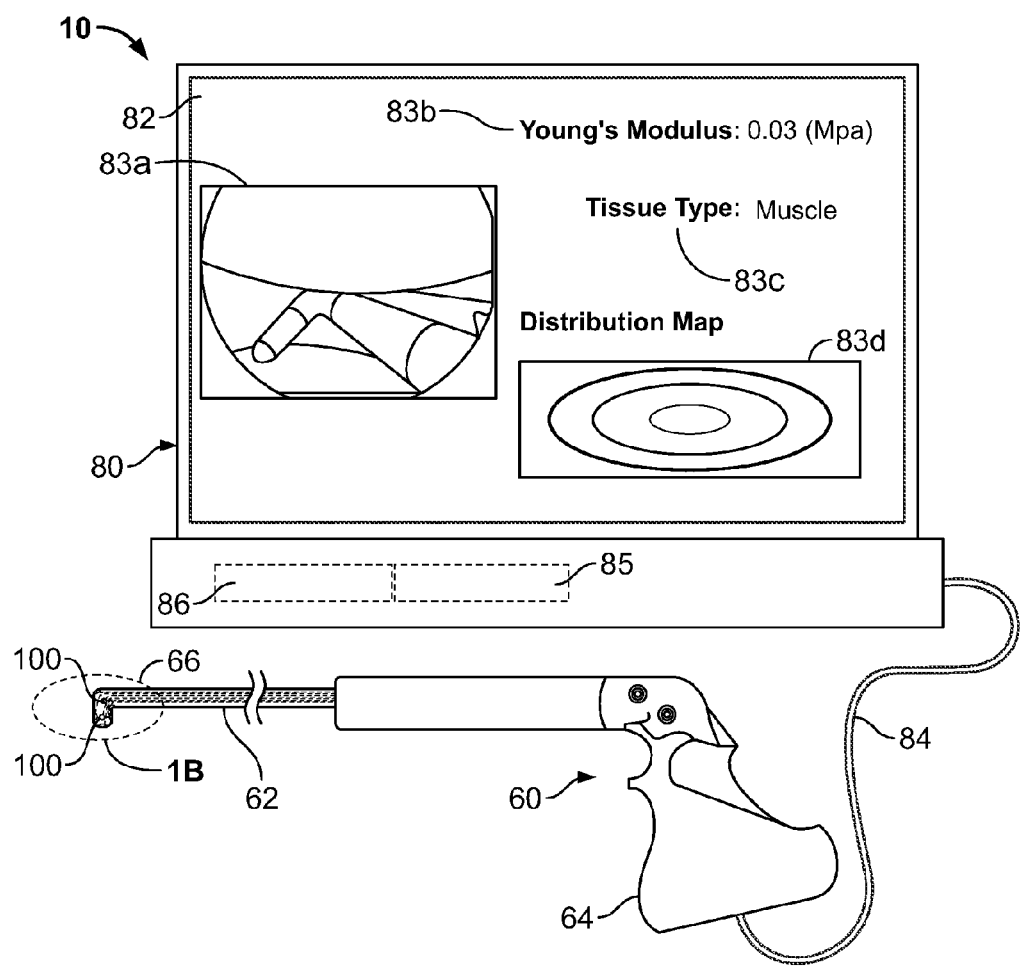
FIGS. 1A-B show one exemplary medical system equipped with one or more tissue elasticity sensors.
Figure 1B:
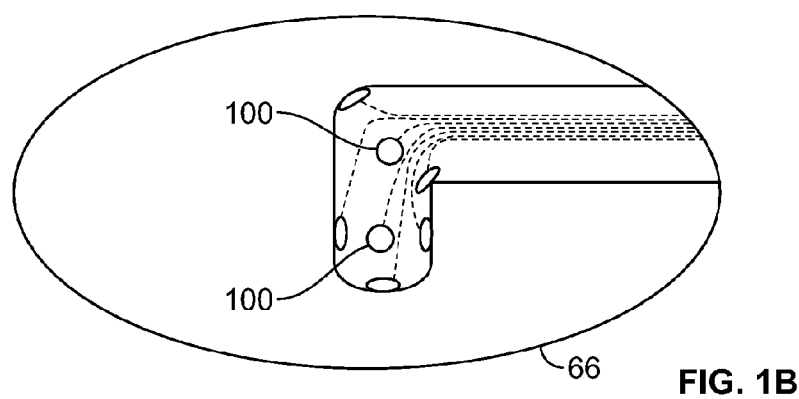

Referring to FIGS. 1A-B, a medical system 10 may include one or more tissue elasticity sensors 100 arranged on a medical instrument 60. In this embodiment, the medical instrument 60 is an arthroscopic tool that can be used to measure cartilage elasticity modulus. The arthroscopic tool 60 can include a probe 62 and a handle 64. The tissue elasticity sensors 100 may be electrically coupled to a control unit 80 so as to provide real-time information to a surgeon or other user. For example, the control unit 80 may include a display device 82 that may provide video imaging 83a of the probe 62 or other graphics while the surgeon maneuvers the probe 62 toward a targeted tissue site. The display device 82 can also output information indicative of type of tissue 83c, a measurement indicative of tissue elasticity 83b, or both. For example, the control unit 80 may receive sensor signals from the tissue elasticity sensors 100 and thereafter output a measurement of the tissue elasticity (e.g., the Young's modulus in this embodiment, the shear modulus in other embodiments, or both the Young's modulus and the shear modulus in further embodiments) and a determination of the type of tissue in contact with the sensors. As described in more detail below, the medical instrument 60 may be equipped with an array of the tissue elasticity sensors 100 so that the control unit 80 can display a map 83d of tissue elasticity measurements along a portion of the medical instrument 60.

As shown in FIG. 1B, the tissue elasticity sensors 100 can be arranged at selected locations of a distal tip portion 66 of the probe 62. The sensors 100 may have a micro-fabricated structure (described in more detail below) that can be bonded or otherwise mounted to an external surface of the tip portion 66. One or more leads may extend from the sensors 100 so as to provide electrical communication to a cable 84 of the control unit 80. As such, sensor signals from the sensors 100 can pass through the leads and the cable 84 to a processor 85 of the control unit 80. The sensor data can be stored in a computer-readable memory device 86 of the control unit. The processor 85 can execute instructions stored on the computer-readable memory device 86 of the control unit 80. The memory 86 can also store the tissue elasticity, force and displacement measured by the sensors 100. The control unit 80 can also include an input device such as a keyboard, mouse or touch screen display to receive user input.

As described in more detail below, each sensor 100 may include a micro-electro-mechanical (MEMS) structure that can provide feedback information indicative of the elasticity of a tissue, the force applied on the tissue, the displacement experienced by the tissue, the proximity between the sensor and the tissue, or a combination thereof. For example, the sensor 100 may include two or more flexible membranes that can have different stiffness properties, as described in more detail below in connection with FIGS. 3-4. Each membrane may separate two electrodes so as to define a capacitive gap therebetween. As the sensor 100 pushes against a tissue, the membranes may have different deflections due to their different levels of stiffness. In such circumstances, the tissue elasticity can be determined from relative displacement of the sensing membranes, which can be determined by measuring the capacitance changes between the electrodes separated by each membrane.

Figure 2A:
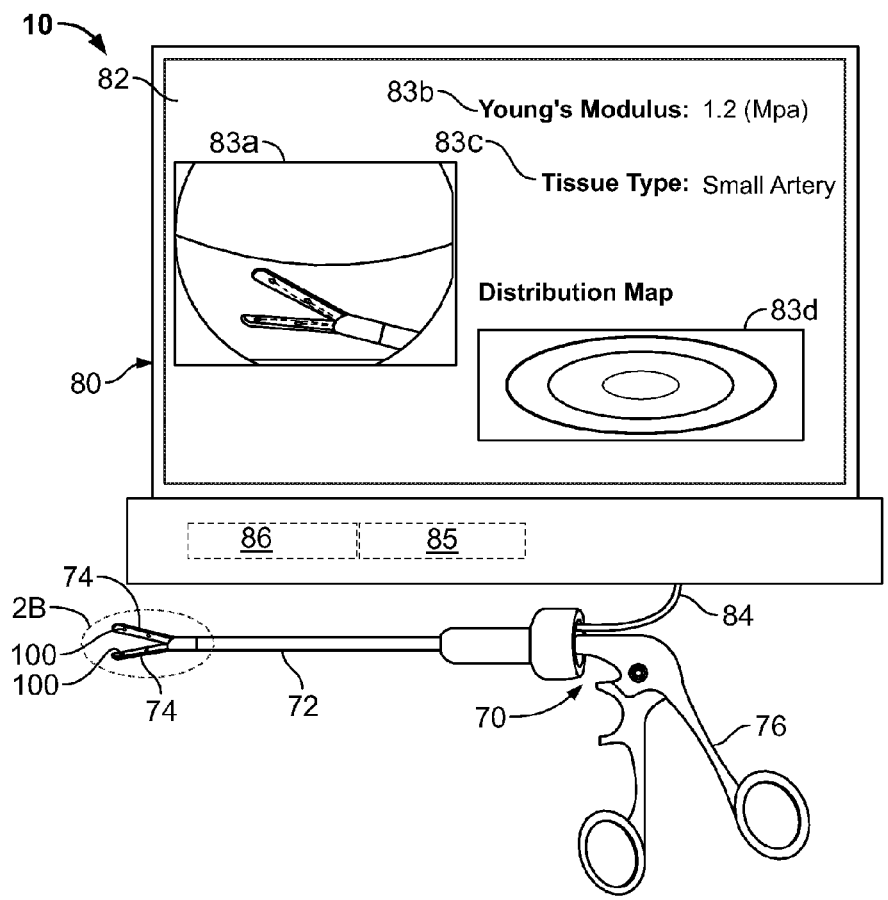
FIGS. 2A-B show another exemplary medical system equipped with one or more tissue elasticity sensors.
Figure 2B:
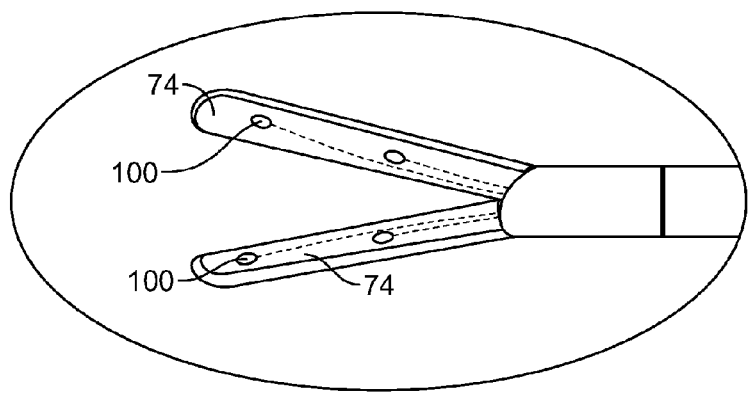

Referring now to FIGS. 2A-B, it should be understood that the medical system 10 is not limited to the tool 60 depicted in FIGS. 1A-B. For example, alternative embodiments of the medical system 10 may include one or more tissue elasticity sensors 100 disposed on an endoscopic tool 70 that can be used to engage target tissue. In this example, the endoscopic tool 70 can include a grasper 72 that has two jaws 74 and an actuator handle 76 that can open and close the jaws 74. The tissue elasticity sensors 100 may be electrically coupled to a control unit 80 so as to provide real-time information to a surgeon or other user via a display device 82. As previously described, the information outputted by the display device 82 may include video imaging 83a of the grasper 72, output information indicative of type of tissue 83c in contact with the sensors 100, measurements 83b indicative of the elasticity of tissue in contact with the sensors 100 (e.g., the Young's modulus in this embodiment, the shear modulus in other embodiments, or both the Young's modulus and the shear modulus in further embodiments), a map 83d of tissue elasticity or an area of the tool 70, or a combination thereof.

As shown in FIG. 2B, the tissue elasticity sensors 100 can be mounted at selected locations on the two opposing surfaces of the grasper jaws 74. Similar to previously described embodiments, the sensors 100 can be electrically connected to a cable 84 of the control unit 80 so as to transmit sensor signals to a processor 85 of the control unit 80. Each sensor 100 may include two or more capacitive membranes with different stiffness (described in more detail below). When the sensor 100 is pushed against a tissue, each membrane can undergo a different amount of deformation that may be determined by the stiffness of that membrane. The tissue elasticity measurement can be determined from relative deflection of the sensor membranes, and the change in capacitance may provide a measure of membrane displacement.

Accordingly, it should be understood from the description herein that tissue elasticity sensors 100 can be coupled to any of a number of different medical instruments for use in procedures in which knowledge of tissue elasticity and force measurements may be useful. For example, the tissue elasticity sensors 100 can be arranged on an arthroscopic tool 60, an endoscopic tool 70, a catheter, or another minimally invasive instrument to provide tissue elasticity information or tissue type information during minimally invasive surgery. In another example, sensors 100 can be arranged on a minimally invasive tool to determine ligament tension during joint surgery (e.g., knee implant surgery or the like) based on the ligament stiffness measured. In yet another example, sensors 100 can be arranged on a minimally invasive tool to aid in a procedure for early detection of compartment syndrome, which can be especially useful in military medical applications or patient transport applications. In still another example, sensors 100 can be arranged on a minimally invasive tool to provide cartilage hardness measurements. In a further example, sensors 100 can be arranged on a robotic gripper for handling tissues. Feedback information indicative of tissue elasticity or type can be used in control algorithms for the robotic gripper so as to improve tissue handling. In another example, sensors 100 can be used to monitor varying elasticity of tissue through its tactile features so as to make early detection of cancerous tumors. In yet another example, an array of sensors 100 can be used to classify the texture of a surface and to map the pressure and elasticity distribution of an object. In still another example, an array of the sensors 100 can be embedded into an artificial skin implant that may simulate the tactile sensory perception of a real skin. In a further example, sensors 100 can provide tissue elasticity measurements so as to aid in the making of implants that may have the same or similar level of stiffness as the tissue in which the implants are embedded. In yet another example, an array of the sensors 100 can be formed as a large flexible substrate that can be mounted to contoured portions of a surgical instrument so as to provide a spatial map of tissue elasticity properties over an entire area of targeted tissue as a function of the location in the targeted tissue site. Such a configuration may be useful, for example, in measuring foot or sole properties for diabetic/podiatry applications, measurement of bed ulcers, an in other applications.

Figure 3:
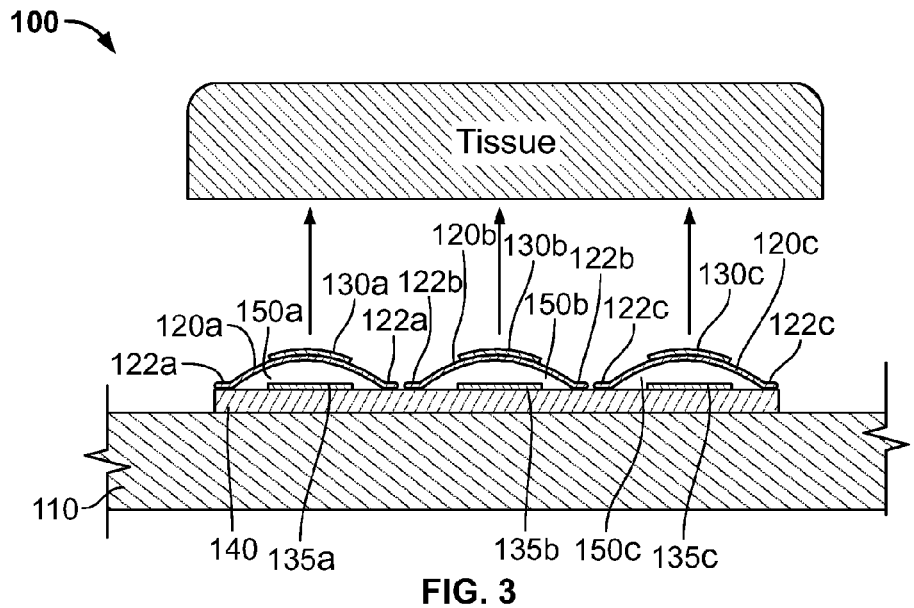
FIG. 3 is a cross-sectional view of a portion of the tissue elasticity sensor of FIGS. 1A-B or FIGS. 2A-B.
Figure 4:
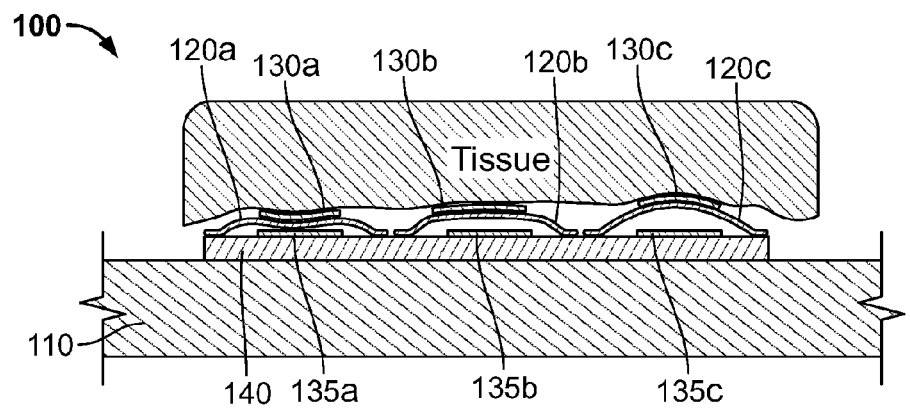
FIG. 4 is a cross-sectional view of the portion of the tissue elasticity sensor of FIG. 3 in contact with a tissue.

Referring now to FIGS. 3-4, some embodiments of the tissue elasticity sensor 100 can be used to measure tissue elasticity without the use of either a controlled force or a controlled displacement. The sensor 100 may be bonded or otherwise mounted to a rigid substrate 110 such as a distal tip portion of a medical instrument (refer, for example, to FIGS. 1B and 2B). The sensor 100 can include a plurality of sensing membranes 120a-c that have different stiffness characteristics. In this embodiment, membrane 120a is a relatively soft membrane that has the lowest stiffness characteristic, membrane 120c is a relatively firm membrane that has the highest stiffness characteristic, and membrane 120b is an intermediate membrane that has a stiffness characteristic between membranes 120a and 120c. Each membrane 120a-c has an electrode 130a-c that is disposed on top of the membrane 120a-c. A periphery 122a-c of each membrane 120a-c is attached onto the substrate 140. The substrate has an electrode 135a-c disposed thereon corresponding to each of the membrane electrodes 130a-c. The membranes 120a-c separate electrodes 130a-c and 135a-c respectively to define capacitive gaps 150a-c between the electrodes 130a-c and 135a-c. Accordingly, when a contact force is applied to the sensor 100, each of membranes 120a-c can be differently displaced and thereby change the capacitive gap 150a-c associated with the deflected membrane 120a-c. The change in the capacitive gaps 150a-c can change the capacitance between the respective electrodes pair 130a-c and 135a-c associated with that deflected membrane 120a-c. As such, signals indicative of the capacitance change can be transmitted via the leads to the control unit for purposes of determining tissue properties, such as a tissue elasticity modulus, a tissue stiffness value, a type of tissue in connect with the sensor, or the like.

For example, as shown in FIG. 4, the membranes 120a-c have different magnitudes of deflection in response to the contact force between the sensor 100 and the tissue. Membrane 120a, which has the lowest stiffness characteristic, undergoes the largest deflection as membrane 120a. Membrane 120c experiences the lowest deformation as membrane 120c has the highest stiffness, and membrane 120b has a displacement that is in between membranes 120a and 120c. In this embodiment, the response of the tissue can be determined from relative displacement of the membranes 120a-c because the sensor 100 is attached onto a rigid substrate 110 that is not substantially displaced when contacted by the tissue. As previously described, the relative displacement may be determined from relative change in capacitances between the electrodes 130a-c and 135a-c that are separated by the membranes 120a-c, respectively.

As described in more detail below, when the footprint of the sensor 100 is significantly smaller than the tissue being contacted, the elasticity modulus of the tissue can be determined (e.g., by the control unit 80 in this embodiment) as a function of the ratio of the stresses of the tissue areas that are in contact with the sensing membranes 120a-c. For example, one model can be derived by considering the tissue as an elastic semi-infinite space, which is reasonable in scenarios where the sensors 100 are micro-fabricated to have a small size (substantially smaller than the tissue that is being contacted). For example, the sensing membranes 120a-c may have a size of 200 μm to 400 μm, which can be generally much smaller than the area of the bodily tissue under contact. This may permit the relationship between the sensor 100 and the tissue to be characterized according to a Boussinesq's model, which describes a concentrated/distributed force acting on an elastic semi-infinite space. In this example, the two circular membranes 120a and 120c with different diameters act as two springs with different spring constants that result in two circular contact areas with different stresses $\sigma_1$ and $\sigma_2$. Also, the deflection of the center region of each membrane is expected to be less than the edges of the membrane due to the metal electrodes in the center of the membranes. This adjustment to the deflection at the center region of each membrane can be approximated and verify using an FEM analysis. In sum, after substituting all the parameters for this particular example, the value of the tissue elasticity modulus ($E_t$) can be determined by:

$$E_t = \frac{(1-v^2)a\left[\left(-11.8+\frac{2.0}{a}\right)+\left(10.8-\frac{2.0}{a}\right)\frac{\sigma_1}{\sigma_2}\right]}{\frac{A_p a^4}{E_m h^3}\left(5.1\frac{\sigma_1}{\sigma_2}-1\right)}$$

where $E_m$ is the Young's Modulus of the membrane, where v is the Poisson's ratio of the membrane material, where a is the unit length (100 μm in the case shown in FIG. 5), where h is the membrane thickness, where $A_p$ is the stiffness coefficient which depends on the size of the center region of the membrane, and where $\sigma_1$ and $\sigma_2$ represent the stresses of the contact area. In some aspects, the stiffness coefficient $A_p$ can be determined from the following equation:

$$A_p = \frac{3(1-\mu^2)}{16}(1-\alpha^4-4\alpha^2\ln\alpha),$$

where α is solidity ratio.

Based on this calculation for the tissue elasticity modulus ($E_t$), the teaching herein indicates that the tissue elasticity modulus ($E_t$) can be determined as a function of the ratio of the stresses ($\tau_1/\sigma_2$), which may be measured from relative deflection of the sensor membranes (as detected, for example, by the change in capacitance of each capacitive gap. In some circumstances, the measurement of elasticity modulus may be preferable over a measured stiffness value because the elasticity modulus may be an inherent property that is independent of tissue geometry. Alternatively, if the size of the sensor 100 may substantially similar to the size of the tissue being contacted (e.g., a small vessel with a diameter less than 1 mm), the sensor 100 can be configured to provide a measurement of the tissue stiffness K value.

Figure 5A:
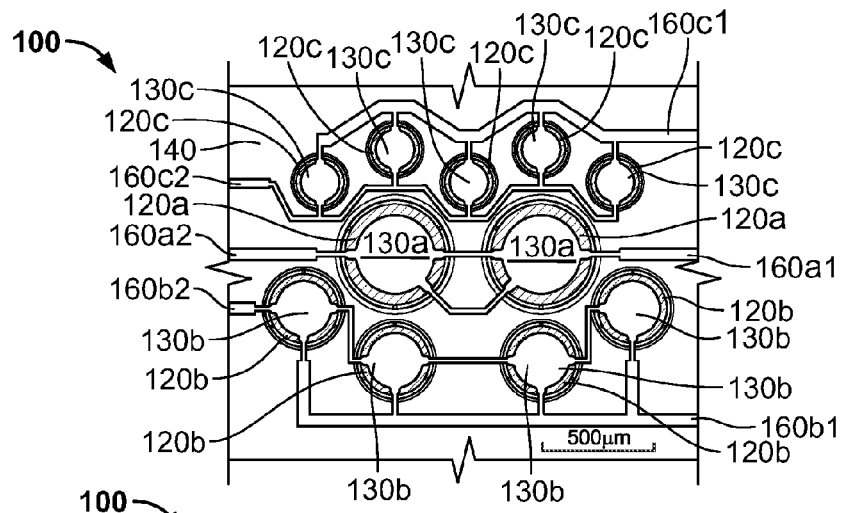
FIGS. 5A-C are top views of three exemplary tissue elasticity sensors having two or more sets of sensing membranes.
Figure 5B:
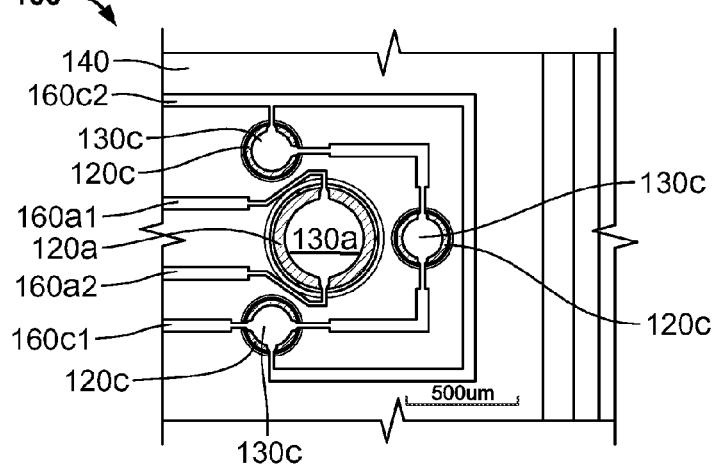
Figure 5C:
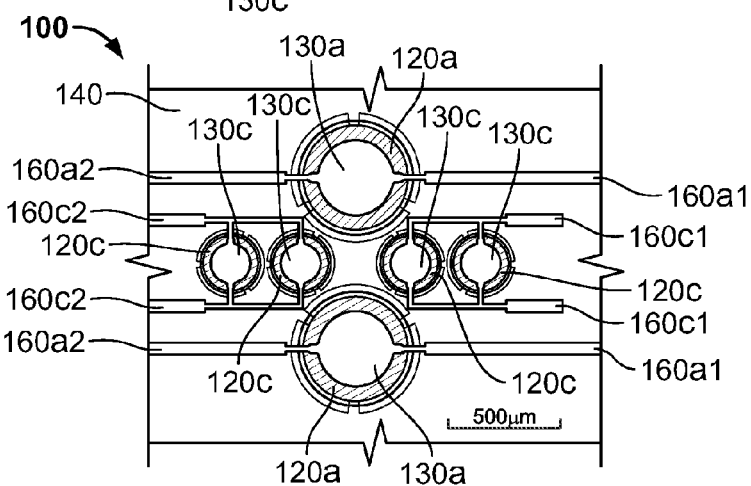

Referring now to FIGS. 5A-C, each tissue elasticity sensor 100 may include two or more sets of sensing membranes 120a-c that can be attached to a common substrate 140. In one embodiment depicted in FIG. 5A, the micro-fabricated sensor 100 can include three sets of membranes 120a-c of different sizes. In another embodiment depicted FIG. 5B, the micro-fabricated sensor 100 can include two sets of membranes 120a and 120c of different sizes. Similarly, in the embodiment depicted FIG. 5C, the micro-fabricated sensor 100 can include two sets of membranes 120a and 120c of different sizes. Within each membrane set, the membranes are substantially in the same size. For example, membranes 120a of FIG. 5A, 5B or 5C may have substantially similar sizes (e.g., about 400 μm in diameter), membranes 120b of FIG. 5A may have substantially similar sizes (e.g., about 300 μm in diameter), and membranes 120c of FIG. 5A, 5B or 5C may have substantially similar sizes (e.g., about 200 μm in diameter). For different membrane sets, the membranes have different sizes. For each sensor 100 in FIG. 5A, 5B, or 5C, the total area of the first set of membranes 120a may be approximately equal to the total area of the second set of membranes 120b and may also be approximately equal to the total area of the third set of membranes 120c. The approximately equal total membrane areas may help maintain a similar resolution (e.g., in terms of capacitive readouts) for each set of membranes.

When membranes are made from the same material, a smaller-sized membrane (e.g., 120c) can have a higher stiffness than a larger-sized membrane (e.g., 120a) and vice versa. For the membranes 120a-c shown in FIG. 5A, membranes 120a can be most compliant because membranes 120a have the largest size; membranes 120c can be the least compliant because membranes 120c have the smallest size; and membranes 120b can have a stiffness value that is in between membranes 120a and 120c because membranes 120b have a size that intermediate to membranes 120a and 120c. For membranes 120a and 120c shown in FIG. 5B or 5C, membranes 120a can have a lower stiffness than membranes 120c since membranes 120a are larger in size than membranes 120c.

Still referring to FIGS. 5A-C, an electrode can be disposed on each membrane. For example, electrode 130a can be disposed on top of each membrane 120a of FIG. 5A, 5B or 5C, electrode 130b can be disposed on top of each membrane 120b of FIG. 5A, and electrode 130c can be disposed on top of each membrane 120c of FIG. 5A 5B or 5C. Underneath each membrane, another electrode can also be disposed on the substrate 140. As previously described in connection with FIG. 3, the two electrodes 130 and 135 associated with each membrane can be separated by a capacitive gap 150 that is defined by the membrane. For each membrane within any membrane set, the two electrodes associated with that membrane may be separately connected to a common pair of leads so that the capacitance of that membrane set can be readily detected. For example, the two electrodes of each membrane 120a of FIG. 5A, 5B or 5C can be connected to leads 160a1 and 160a2 respectively, the two electrodes of each membrane 120b of FIG. 5A can be connected to leads 160b1 and 160b2 respectively, and the two electrodes of each membrane of FIG. 5A, 5B or 5C can be connected to leads 160c1 and 160c2 respectively. As such, each membrane set 120a, 120b, or 120c can form a parallel capacitor array so that the capacitance readout from each membrane of that membrane set can be added together to provide the deflection for that membrane set. A greater number of smaller membranes may be used so that the total area of smaller membranes is comparable to the larger membranes. This may make the capacitive readout of smaller membranes comparable to larger membranes. For example, in FIG. 5A, five smaller membranes 120c are used, as compared to four for larger membrane 120b and two for largest membrane 120a; in FIG. 5B, three smaller membranes 120c are used, as compared to one for larger membrane 120a; and in FIG. 5C, four smaller membranes 120c are used, as compared to two for larger membrane 120a.

Figure 6:
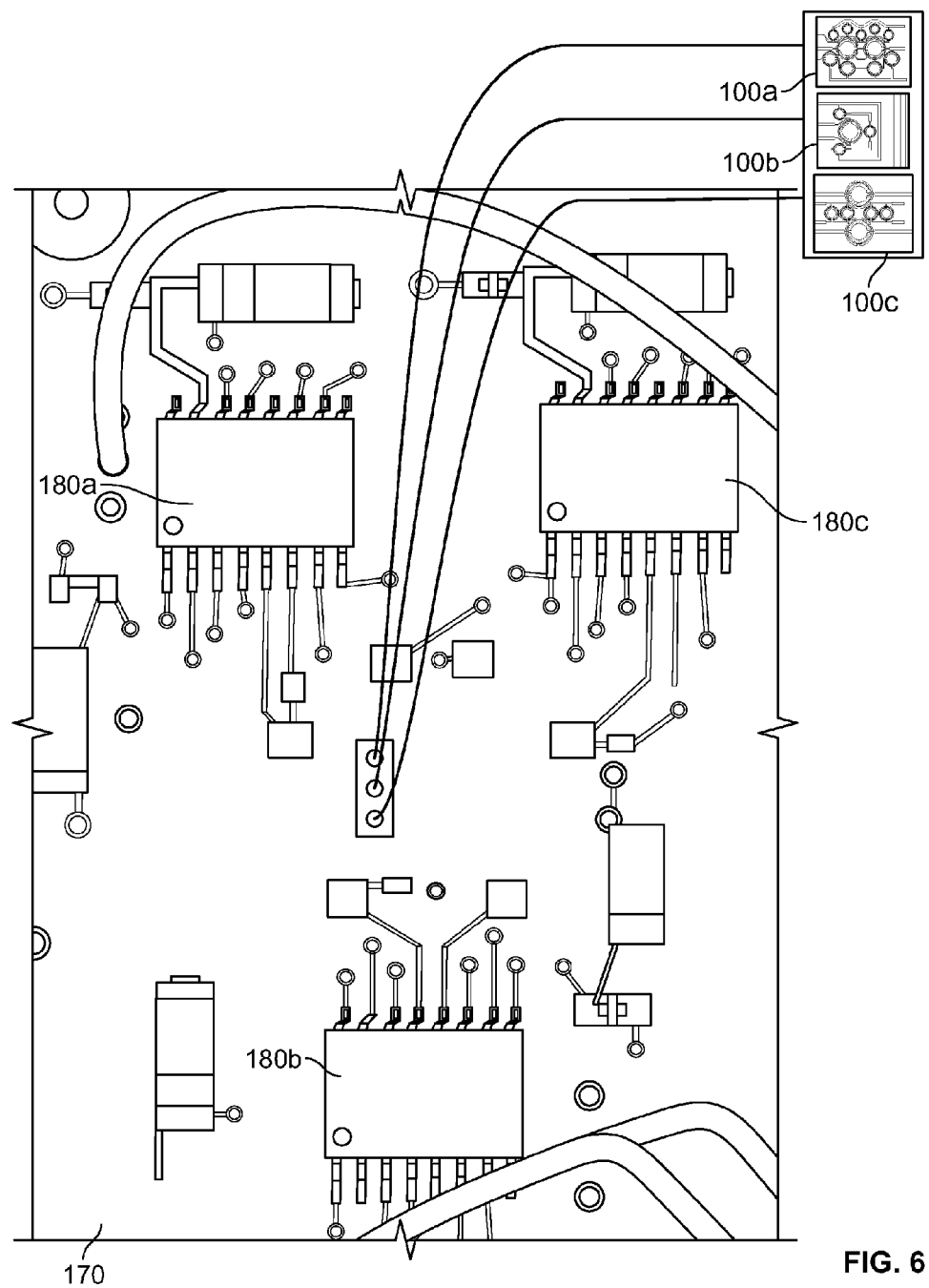
FIG. 6 shows the three exemplary tissue elasticity sensors of FIGS. 5A-C disposed on a substrate and in communication with a circuit to process sensor signals.

Referring now to FIG. 6, three tissue elasticity sensors 100a-c having the same membrane configurations as the three sensors embodiments shown in FIGS. 5A-C are disposed on a sensor array that is electrically coupled to a controller circuit 170. The controller circuit 170 may be incorporated into the control unit 80 (FIGS. 1A and 2A) or another unit, and the controller circuit 170 can be configured to process sensor signals from the sensors 100a-c. In this embodiment, the first sensor 100a has the same configuration as sensor embodiment shown FIG. 5A, the second sensor 100b has the same configuration as sensor embodiment shown in FIG. 5B, and the third sensor 100c has the same configuration as sensor embodiment shown in FIG. 5C. The controller circuit 170 can include one or more integrated circuit (IC) chips that are configured to measure capacitance between the previously described electrode pairs 130a-c and 135a-c respectively. In this embodiment, the controller circuit 170 includes three capacitance measurement chips 180a-c. In one example, each IC chip 180a-c can be connected to the three sensor 100a-c to measure the capacitance of that particular membrane set. For instance, the IC Chip 180a receives signals indicative of the capacitance of the membrane set with the smallest membranes 120a; the IC chip 180c measures the capacitance of the membrane set with the largest membranes 120c; and the IC chip 180b measures the capacitance of the membrane set with the intermediate membranes 120b.

Referring now to FIGS. 7A-G, a tissue elasticity sensor 100 can be micro-fabricated using chemical vapor deposition and etching processes. In some embodiments, the fabrication process can start with a silicon wafer 200. The silicon wafer 200 can be coated with a silicon nitride (SiNx) layer 210 for passivation (FIG. 7A). The SiNx layer may be coated using plasma enhanced chemical vapor deposition (PECVD). In some implementations, the SiNx layer 210 may have a thickness of about 300 nm to about 1000 nm, and about 600 nm in this embodiment. A Cr—Au metal layer 220 can then be E-beam evaporated to form a bottom electrode (FIG. 7B). In some implementations, the bottom electrode 220 may have a thickness of about 200 nm to about 500 nm, and preferably about 260 nm in this embodiment. A sacrificial aluminum layer 230 can be E-beam deposited and patterned via wet etching (FIG. 7C). In some implementations, the sacrificial aluminum layer 230 may have a thickness of about 600 to about 2500 nm, and preferably about 800 nm to about 1800 nm in this embodiment. Another SiNx layer 240 can then be deposited by PECVD to form a sensing membrane (FIG. 7D). In some implementations, the membrane 240 may have a thickness of about 300 nm to about 1500 nm, and preferably about 500 nm to about 1000 nm in this embodiment. A top electrode can be patterned by wet etching a Cr—Au E-beam evaporated metallization layer 250 (FIG. 7E). In some implementations, the top electrode 250 may have a thickness of about 30 nm to about 500 nm, and preferably about 40-200 nm in this embodiment. Etch holes 260 can then be patterned via dry plasma etch (FIG. 7F). The sacrificial Al layer 230 can be etched in wet etching solution and the membrane 240 can be released in a critical point dryer to provide an embodiment of the stiffness sensor 100 (FIG. 7G).

Figure 8A:
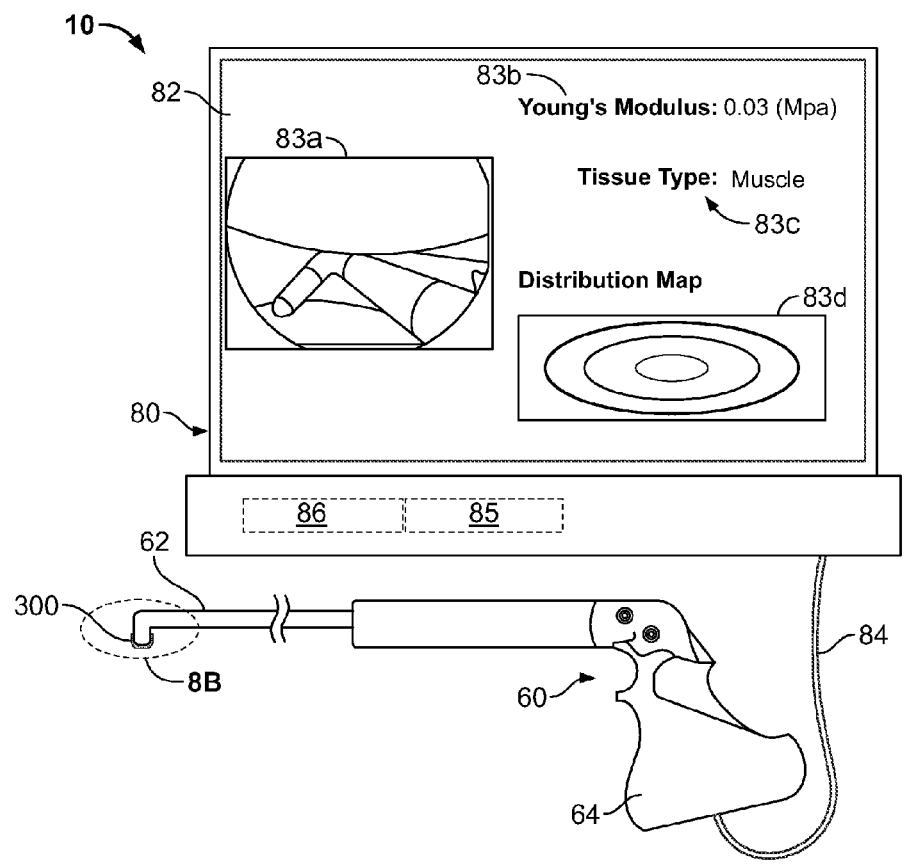
FIGS. 8A-B show one exemplary medical system equipped with a flexible substrate having an array of tissue elasticity sensors.
Figure 8B:
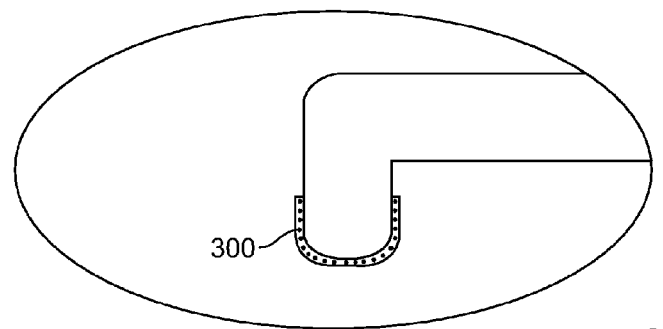

Referring now to FIGS. 8A-B, another embodiment of the medical system 10 may include at least one flexible substrate 300 that provides an array of tissue elasticity sensors 100. The flexible substrate 300 can be contoured around a curved portion of a medical instrument 60 at selected locations. In this embodiment, the medical instrument 60 is an arthroscopic tool that can include a probe 62 and a handle 64. The flexible substrate 300 having the array of tissue elasticity sensors 100 may be electrically coupled to a control unit 80 so as to provide real-time information to a surgeon or other user. Similar to previously described embodiments, the control unit 80 may include the display device 82 that can provide video imaging 83a or other graphics of the probe 62 while the surgeon maneuvers the probe 62 toward a targeted tissue site. The display device 82 can also output information indicative of tissue type 83c or tissue elasticity 83b (e.g., the Young's modulus in this embodiment, the shear modulus in other embodiments, or both the Young's modulus and the shear modulus in further embodiments). In this embodiment, the control unit 80 is configured to receive sensor signals from the tissue elasticity sensors 100 that are embedded in each flexible substrate 300 and thereafter output a measurement of the tissue elasticity modulus (e.g., Young's modulus and/or shear modulus), a map 83d of the tissue elasticity distribution along the array of sensors 100, and a determination of the tissue type 83c.

As described in more detail below, each flexible sheet 300 may include two sets of electrodes. The two electrode sets can be arranged in generally orthogonal directions. Each intersection of the electrodes can be separated by a capacitive gap so as to define at least a portion of one tissue elasticity sensor 100. Accordingly, the flexible sheet 300 may have an array of tissue elasticity sensors 100 that can collectively measure the elasticity of a targeted tissue, the force and/or displacement imparted to the targeted tissue, and the spatial distribution of the tissue elasticity in both normal and shear directions. Each electrode may have one or more leads extending therefrom so as to electrically connect the stiffness sensors 100 to the cable 84 of the control unit 80. Sensor signals from the sensors 100 can pass through the leads and the cable 84 to the processor 85 of the control unit 80. The memory 86 can also store the feedback information indicative of the elasticity of a targeted tissue and the force and/or displacement imparted to the targeted tissue.

Figure 9A:
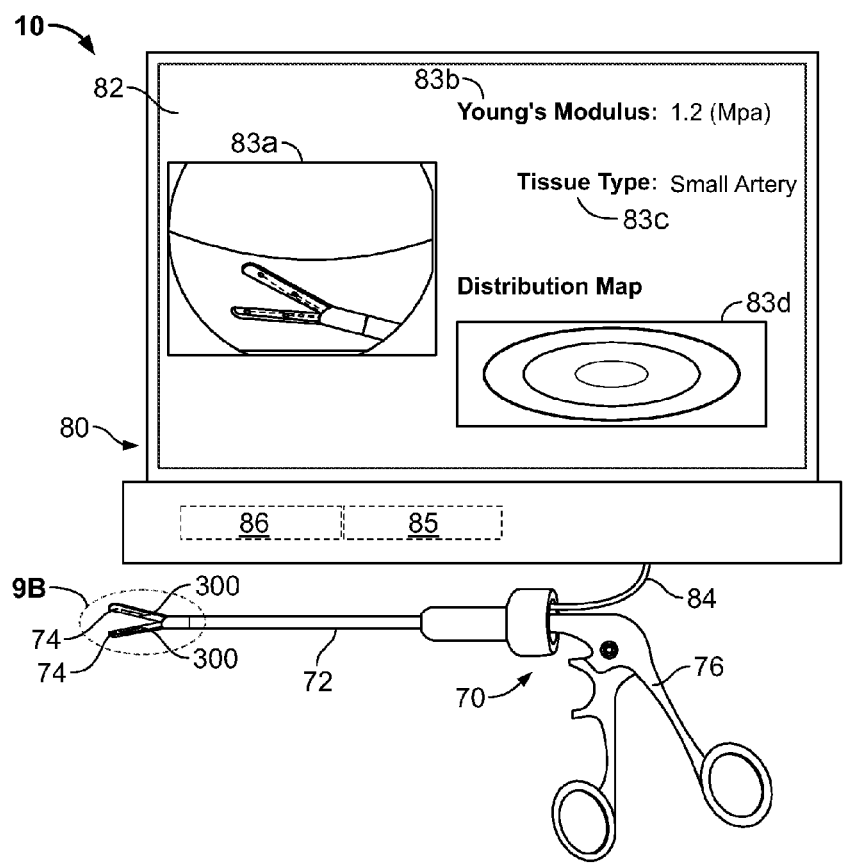
FIGS. 9A-B shows another exemplary medical system equipped with a flexible substrate having an array of tissue elasticity sensors.
Figure 9B:
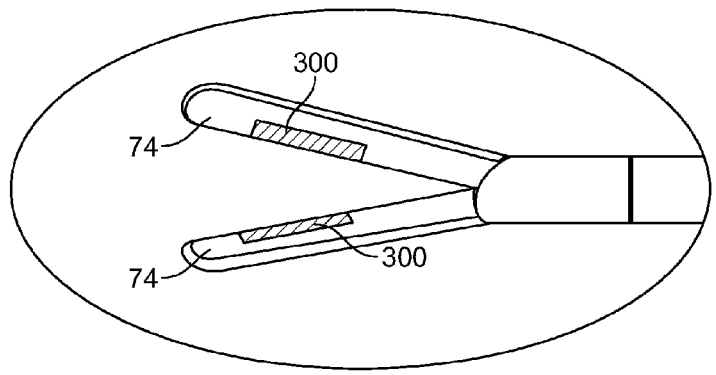

Referring now to FIGS. 9A-B, the medical system that employs the flexible substrate 300 having the array of tissue elasticity sensors 100 is not limited to the probe 60 described in connection with FIGS. 8A-B. For example, one or more flexible substrates 300 can be mounted to contoured surfaces of an endoscopic tool 70 at selected locations. In this embodiment, the endoscopic tool 70 can include a grasper 72 that has two jaws 74 and a handle 76 that can open and close the jaws 74. The flexible sheets 300 with the array of stiffness sensors 100 may be electrically coupled to the control unit 80 so as to provide real-time information to a surgeon or other user via the display device 82. Similar to previously described embodiments, the control unit 80 may include the display device 82 that can provide video imaging 83a or other graphics of the grasper 72 that advances toward a targeted tissue site. The display device 82 can also output information indicative of tissue type 83c or tissue elasticity 83b. In this embodiment, the control unit 80 is configured to receive sensor signals from the tissue elasticity sensors 100 that are embedded in each flexible substrate 300 and thereafter output a measurement of the tissue elasticity modulus (e.g., Young's modulus, the shear modulus, or both), a map 83d of the tissue elasticity distribution along the array of sensors 100, and a determination of the tissue type 83c.

Accordingly, it should be understood from the description herein that the flexible substrate 300 having the array of tissue elasticity sensors 100 can be used with a variety of medical instruments in procedures where knowledge of tissue type, stiffness, force and/or displacement may be useful. For example, the flexible substrate 300 having the array of tissue elasticity sensors 100 can be arranged on a minimally invasive instrument such as an arthroscopic tool 60 and an endoscopic tool 70 to provide real-time information indicative of tissue type or stiffness. In another example, the flexible substrate 300 having the array of tissue elasticity sensors 100 can be mounted to contoured portions of a medical instrument so as to provide a spatial map of tissue elasticity properties over an entire area of targeted tissue as a function of the location in the targeted tissue site. Such a configuration may be useful, for example, in measuring foot or sole properties for diabetic/podiatry applications, measurement of bed ulcers, an in other applications. In a further example, the flexible substrate 300 having the array of tissue elasticity sensors 100 can be used to determine ligament tension during joint surgery, make early detection of compartment syndrome, and measure cartilage hardness. Also, the flexible substrate 300 having the array of tissue elasticity sensors 100 can also be use to perform robotics tactile sensing, make early detection of tumors, classify tissue surface texture, fabricate artificial skins, and aid in making of stiffness-matched implants.

Figure 10A:
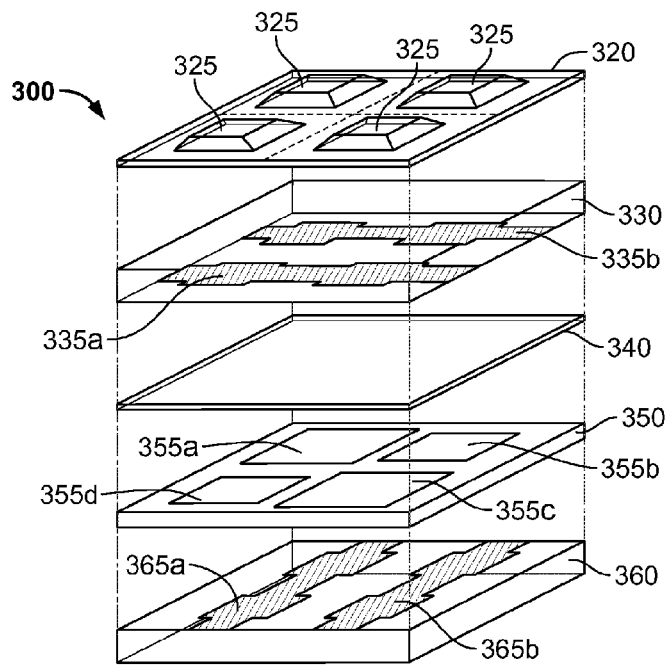
FIG. 10A is an exploded view of a portion of an array of tissue elasticity sensors formed in a flexible sheet.

Referring now to FIG. 10A, some embodiments of the flexible substrate 300 may micro-fabricated from a combination of a plurality of layers. For example, in this embodiment, the flexible substrate can be formed from a combination of a bump layer 320, a top layer 330, an insulation layer 340, a spacer layer 350, and a bottom layer 360. Two parallel top electrodes 335a-b can be disposed on the bottom surface of the top layer 330. Two parallel bottom electrodes 365a-b that are perpendicular to the two top electrodes 335a-b can be disposed on the top surface of the bottom layer 360. The spacer layer 350 can be sandwiched between the top and bottom electrodes 335a-b and 365a-b. The spacer layer 350 includes four openings 355a-d that are arranged in the four areas where the electrodes cross one another. Each opening may define a capacitive gap between the top electrode and the bottom electrode that intersect at the opening. As such, the illustrate portion of the flexible substrate 300 includes a 2×2 array of capacitive gaps adjacent to a respective portion of a membrane layer. In this embodiment, the four openings 355a-d have two different sizes. For example, openings 355a and 355c are generally larger than openings 355b and 355d. Accordingly, the portions of the membrane layer adjacent to the openings 355a and 355c have a larger membrane size and greater compliance. The portions of the membrane layer adjacent to the openings 355b and 355d have a smaller membrane size and thus are relatively less compliant (more stiff). As described in more detail below, when a load is applied to the substrate 300, the more compliant membrane portions (e.g., adjacent to the openings 355a and 355c) may undergo a larger deformation than the less compliant membrane portions (e.g., adjacent to the openings 355b and 355d). In such circumstances, a larger capacitive change can be detected in the more compliant membrane portions (e.g., adjacent to the openings 355a and 355c). The insulation layer 340 can reduce the likelihood of short circuiting some electrodes 335a-b and 365a-b, especially when large deflections may occur. The bump layer 320 may include four bumps 325 that would contact a targeted tissue site when the flexible sensor substrate 300 is directed against the tissue. The four bumps 325 are arranged generally above in the four areas where the electrodes intersect (e.g., proximate to the capacitive gaps) so as to facilitate the deflections of the four capacitive membrane cells.

Figure 10B:
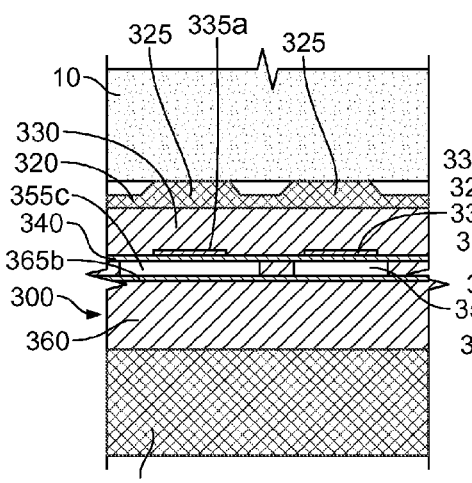
FIGS. 10B-C are cross-sectional views of a portion of the flexible sheet of FIG. 10A mounted on an instrument.
Figure 10C:
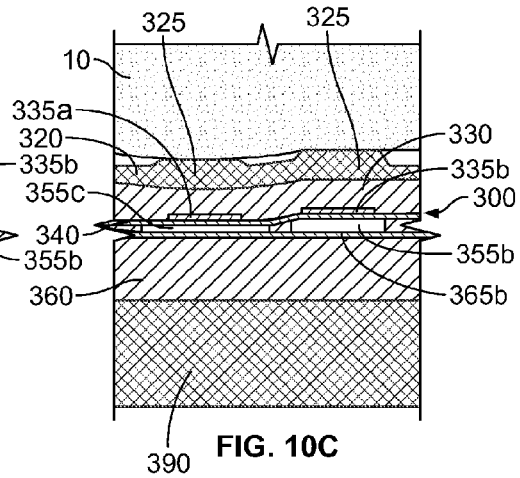

Referring now to FIGS. 10B-C, some embodiments of the flexible substrate 300 can include differently sized capacitive gaps 355b-c (refer also to FIG. 10A) so as to provide different displacements in response to contact between the tissue 10 and the sensor substrate 300. As previously described, each gap 355b-c separates an electrode pair so that the neighboring gaps 355b-c form a pair of sensing capacitors. The gap 355c is larger in size than the gap 355b. As such, the sensing capacitor that is defined by top electrode 335a and bottom electrode 365a (separated by gap 355c) may be more compliant than the sensing capacitor that is defined by top electrode 335b and bottom electrode 365a (separated by gap 355b). When the bumps 325 that are aligned with the gaps 355b-c are urged against the tissue 10, the portion of the membrane layer 330 that is adjacent to the gap 355c can deflect more than the portion of the membrane layer 330 that is adjacent to the smaller gap 355b. As such, the more compliant capacitor can have a larger capacitive change than the less compliant capacitor. Since the flexible sheet 300 is attached to a rigid substrate 390 such as a surface of medical instrument, the stiffness of the tissue can then be determined from relative displacement of different sensing capacitors in the flexible substrate, which can be determined from relative capacitance changes of the differently sized capacitive gaps 355b-c that may be measured using a capacitance measurement unit.

Figure 11:
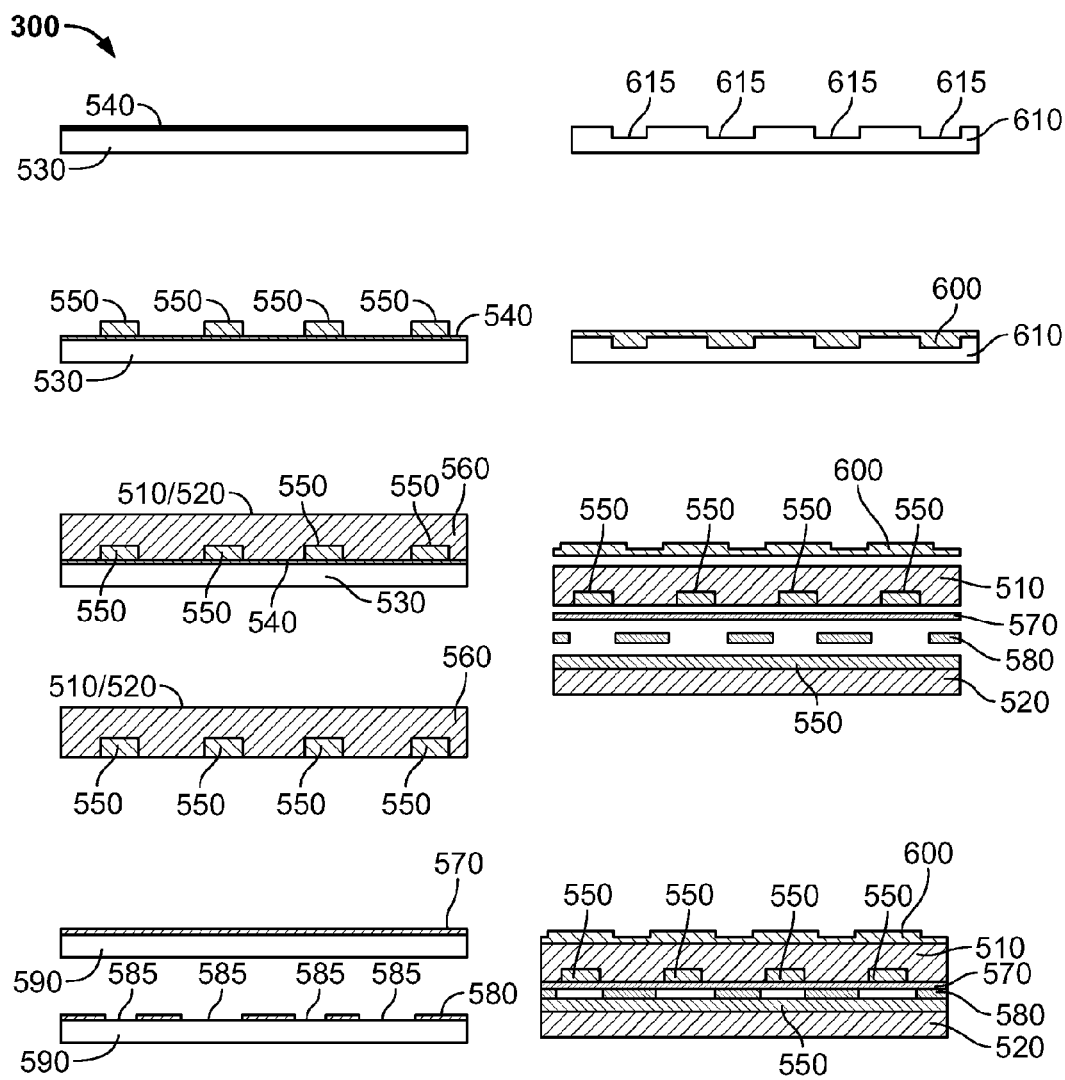
FIG. 11 shows an exemplary process for fabricating a flexible sheet with an array of tissue elasticity sensors.

Referring to FIG. 11, a process for fabricating a flexible substrate 300 having the array of tissue elasticity sensors 100 can include making a top electrode layer 510 and a bottom electrode layer 520. Both the top and the bottom electrode layers 510, 520 can start with a bare silicon wafer 530. The silicon wafer 530 may be coated with a LOR layer 540 (LOR 20B may be supplied from MicroChem Corporation, Newton, Mass.). In some implementations, the LOR layer can have a thickness of about 5 µm to about 15 µm, and preferably about 10 µm in this embodiment. Copper traces 550 can then be electroplated on the LOR layer 540, followed by sputtering an adhesion layer of Ti.

In this embodiment, the flexible substrate 300 may comprise one or more layers of polydimethylsiloxane (PDMS) to define the capacitive gaps. PDMS may have several advantageous properties that can make PDMS sensors suitable for soft tissue medical characterization. For example, PDMS may be flexible, ductile and biocompatible; PDMS can be sterilized for medical applications; and PDMS may be softer than other polymers, such as LCP, polyamide, EPON SU-8, PMMA, Parylene and perfluoro-polymers, that are commonly used in micro-fabrication.

As shown in FIG. 11, after the step of sputtering an adhesion layer of Ti, liquid PDMS 560 (Sylgard 184 available from Dow Corning, Midland, Mich.) can then be spin-coated. The PDMS coating 560 may be cured at room temperature so as to minimize the deformation of the PDMS 560. After curing, the PDMS layer 560 with copper wires 550 embedded therein can be peeled off the silicon wafer 530. The LOR layer 540 can serve as a sacrificial layer that may trigger the peeling of the PDMS layer 560. The peeled PDMS layer 560 can be used as either the top or the bottom electrode layer 510, 520. The above fabrication process may then be repeated to produce either the bottom or the top electrode layer 520, 510.

The sensor sheet fabrication process can also include making an insulation layer 570 and a spacer layer 580 (FIG. 11B). The insulation layer 570 can be fabricated by coating and curing a thin PDMS layer on a silicon wafer 590. In some implementations, the PDMS layer 570 may have a thickness of about 3 µm to about 9 µm, and preferably about 6 µm in this embodiment. The surface of the silicon wafer 590 may be self assembled monolayer (SAM) treated in trichlorosilane vapor (available Sigma-Aldrich) such that the wafer surface can be converted from a hydrophilic surface to a hydrophobic surface. In some implementations, liquid PDMS may be diluted by Hexane solution before spin-coating to control coating thickness. The cured PDMS layer 570 can then be peeled off the silicon wafer 590 to provide the insulation layer 570.

The spacer layer 580 can be fabricated using a process that is similar to the process described above for making the insulation layer 570, except that the cured PDMS layer 580 may be etched to create an array of openings 585 that can substantially resemble the array of the stiffness sensor 100 before the PDMS layer 580 is peeled off the silicon substrate 590 to provide the spacer layer 580. The etched openings 585 in the spacer layer 580 may have different sizes ranging, for example, from about 200 µm×200 µm square openings to about 1000 µm×1000 µm square openings. In some implementations, the spacer layer 580 may be etched 500 µm×500 µm square openings and etched 600 µm×600 µm square openings.

The sensor sheet fabrication process can further include making a bump layer 600 (FIG. 11C). The bump layer 600 can be fabricated by starting with a clean silicon wafer 610 patterned with an array of bump molds 615 that may substantially resemble the array of the stiffness sensors 100. The array bump molds 615 may be etched by DRIE process. The surface of the silicon wafer 610 can also be SAM treated, followed by spin-coating and curing PMDS 600. In some implementations, the PMDS coating 600 can have a thickness of about 50 µm to about 200 µm, and preferably about 100 µm in this embodiment. The cured PMDS layer 600 can then be peeled off the silicon wafer 610 to provide the bump layer 600.

Still referring to FIG. 11, the flexible sensor substrate fabrication process can additionally include aligning the above fabricated layers including electrode layers 510 and 520, insulation layer 570, spacer layer 580 and bump layer 600 and then bond these layers together to form the flexible sensor substrate 300. The fabricated layers may be sequentially aligned on a contact aligner. For example, the top electrode layer 510 and the insulation layer 570 may first be aligned, followed by alignment of the spacer layer 580 and the bottom electrode layer 520. The top electrodes and the bottom electrodes can be arranged perpendicular to one another. The assembly of the top electrode layer 510 and the insulation layer 570 may then be aligned with the bump layer 600, followed by aligning the assembly of the top electrode layer 510, the insulation layer 570 and the bump layer 600 with the assembly of the spacer layer 580 and the bottom electrode layer 520. After the alignment is completed, all the layers may be bonded together to form the flexible sensor sheet 300. In some implementations, all the PDMS layers can be treated with oxygen plasma so as to achieve an inter-layer bonding with desired mechanical property. The etched openings 585 in the spacer layer 580 may separate the intersected top and bottom electrodes to provide capacitive gaps therebetween such that an array of capacitive membranes may be formed to provide the array of tissue elasticity sensors 100.

Figure 12:
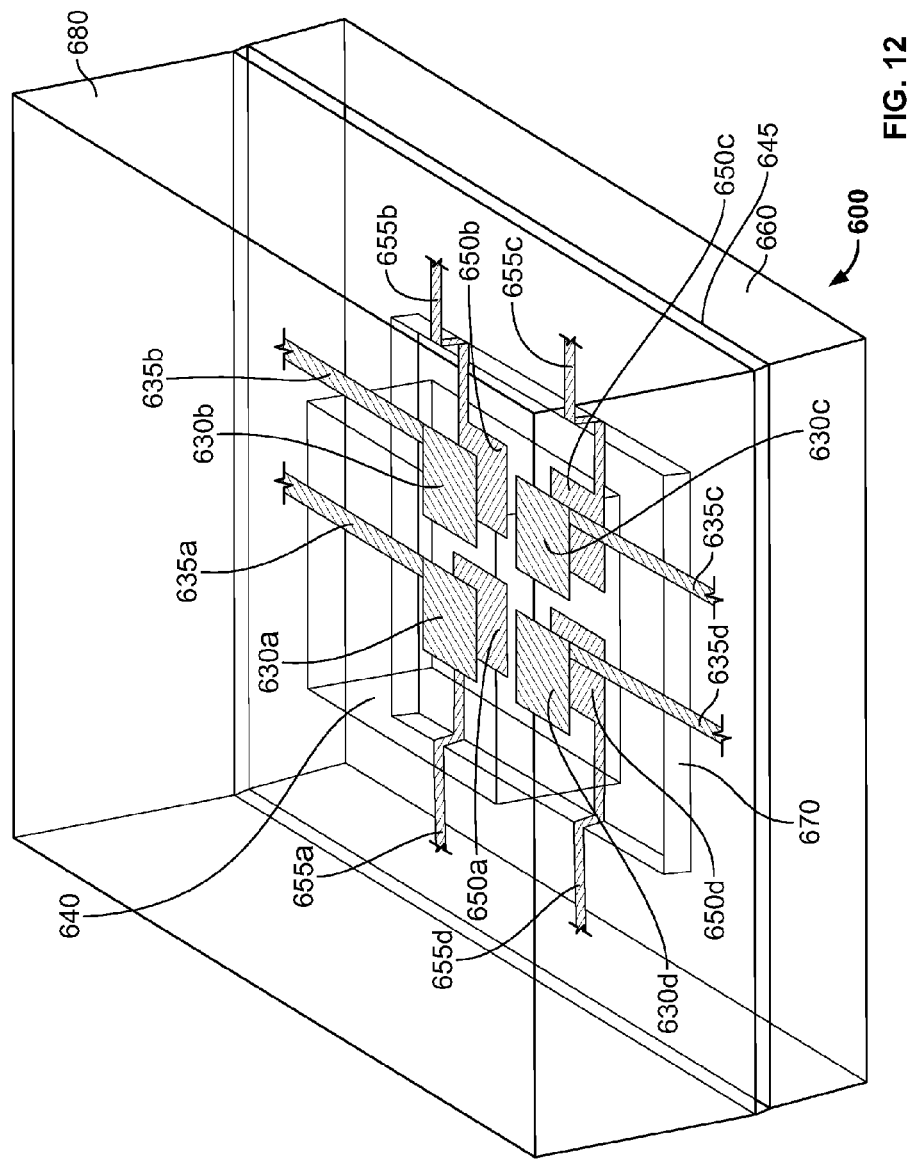
FIG. 12 is perspective view of a tissue elasticity sensor configured to measure shear elasticity and normal elasticity, in accordance with some embodiments.

Referring now to FIG. 12, some embodiments of a tissue elasticity sensor 600 can be configured to sense both normal and shear elasticity characteristics (e.g., in this embodiment, both Young's modulus and the shear modulus of the targeted tissue). Similar to previously described embodiments, the tissue elasticity sensor may be micro-fabricated in an array (e.g., on a flexible or rigid substrate) and bonded to a working end portion of a minimally invasive medical instrument. In the depicted embodiment, each capacitive gap 670 of the sensor 600 may include a plurality of top electrodes 630a-d and a plurality of corresponding bottom electrodes 650a-d. As described below in connection with FIGS. 13A-B, the adjacent electrode pairs in the capacitive gap 670 can be used to detect a shear displacement of the capacitive gap in response to a shear loading. Also, the capacitive gap 670 can deflect differently from a neighboring gap 670 in response to a normal force. Accordingly, the sensor signals from the electrode pairs at each capacitive gap 670 can be received by the control unit 80, which thereafter outputs measurements of both Young's modulus and the shear modulus (or other tissue properties).

As shown in FIG. 12, this embodiment of the tissue elasticity sensor 600 can include four top electrodes 630a-d of about the same size. The top electrodes 630a-d may be disposed on the bottom surface of a silicon mesa 640. The mesa 640 may include a peripheral membrane layer 645 that extends from the mesa 640 and over the peripheral portion of the capacitive gap 670. As described below in FIGS. 13A-B, the peripheral membrane layer 645 of one sensor 600 may have a different thickness than a second neighboring sensor 600. In such circumstances, the capacitive gaps 670 of the first and second sensors 600 may undergo different displacements in response to a normal load or a shear load. Each top electrode 630a-d can have a lead 635a-d extending therefrom so as to connect that top electrode 630a-d to a control circuit for capacitance measurement. The tissue elasticity sensor 600 can also include four bottom electrodes 650a-d of about the same size. The bottom electrodes 650a-d may be disposed on the top surface of a base substrate 660. Each bottom electrode 650a-d can also have a lead 655a-d extending therefrom to connect that bottom electrode 650a-d to the control circuit. The four top electrodes 630a-d and the four bottom electrodes 650a-d can be aligned with one another respectively and separated by the capacitive gap 670 so as to define four sensing capacitors in a quadrant configuration. The tissue elasticity sensor 600 can further include a deposited exterior layer 680 (e.g., comprising rubber, PDMS, or the like) that may have one or more bumps to facilitate the application of shear loads onto the tissue elasticity sensor 600. The rubber layer 680, the silicon mesa layer 640 and the substrate layer 660 can be bonded together provide one or more microfabricated sensors 600. When normal forces are applied on the silicon mesa 640 through the rubber layer 680, all four sensing capacitors may undergo a substantially uniform deflection as the four capacitors have about the same stiffness. When shear loads are applied on the mesa 640 through the rubber layer 680, the four sensing capacitors may experience different deformations as the silicon mesa 640 deflects. This can result in different capacitance changes in the four capacitors which may be used to determine the magnitude of the applied shear loads.

Figure 13A:
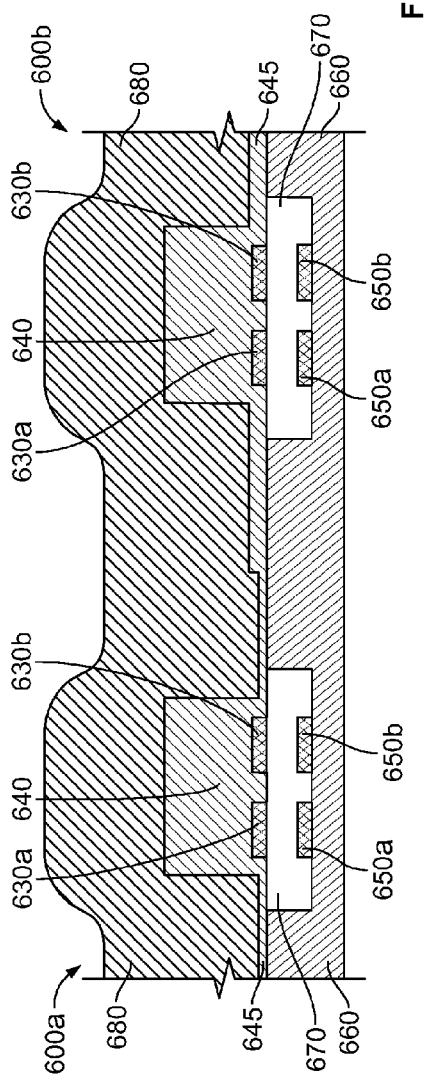
FIG. 13A is a cross-sectional view of the tissue elasticity sensor of FIG. 12.
Figure 13B:
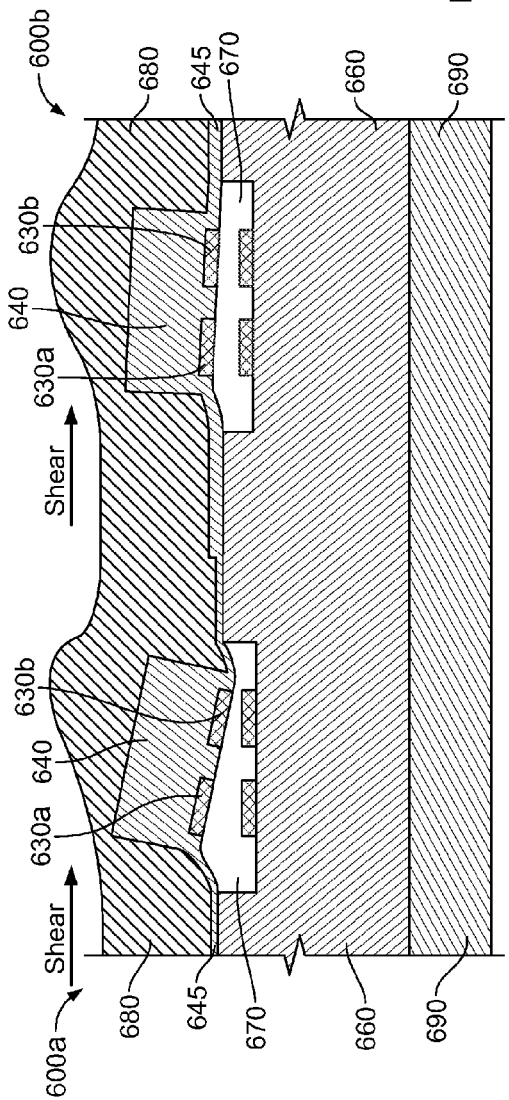
FIG. 13B shows the tissue elasticity sensor of FIG. 13A under shear loading.

Referring now to FIGS. 13A-B, when the tissue elasticity sensor 600 is micro-fabricated in an array, the sensor 600 may be used to measure both normal and shear tissue force and stiffness. As previously described, the array of sensors 600a-b can be bonded or otherwise mounted to a surface 690 of a minimally invasive medical instrument. In the portion of the array depicted in FIG. 13A, the first sensor 600a includes a membrane layer 645 having a smaller thickness than the membrane layer 645 of the second sensor 600b. Accordingly, the capacitive gaps 670 of the first and second sensors 600 may undergo different displacements in response to any of a normal load and a shear load. For example, as shown in FIG. 13B, when the sensor array including the sensors 600a-b undergo a shear load, the first sensor 600a may have a larger shear deflection than the second sensor 600b in the array. This shear deflection of the first sensor 600a can be detected, for example, from the capacitance changes in the first sensor 600a between the first electrode pair 630a and 650a and between the second electrode pair 630b and 650b. Similarly, the this shear deflection of the second sensor 600a (which is less than the first sensor 600a) can be detected, for example, from the capacitance changes in the second sensor 600b between the first electrode pair 630a and 650a and between the second electrode pair 630b and 650b. Accordingly, when the sensor array is pushed against a targeted tissue to create a shear load, each membrane 645 of the two different sensors 600a-b can undergo a different amount of shear deformation that may be determined by the stiffness of that membrane 645. The shear elasticity measurement of the tissue can be determined from relative deflection of the membranes 645 in the first and second sensors 600a-b, and the change in capacitance between the first electrode pair 630a and 650a and between the second electrode pair 630b and 650b in each sensor 600a-b may provide a measure of the membrane displacement. In addition, when the sensor array including the sensors 600a-b undergo a normal load (from contact with the targeted tissue), the first sensor 600a may have a larger normal deflection than the second sensor 600b in the array. This normal deflection of the first sensor 600a can be detected, for example, from the displacement in the first sensor 600a of the first electrode pair 630a and 650a and the second electrode pair 630b and 650b (which may undergo as similar normal displacement). Similarly, the this normal deflection of the second sensor 600a (which is less than the first sensor 600a) can be detected, for example, from the displacement in the second sensor 600b of the first electrode pair 630a and 650a and the second electrode pair 630b and 650b. Similar to previously described embodiments, when the sensor array is pushed against a targeted tissue to create a normal load, each membrane 645 of the two different sensors 600a-b can undergo a different amount of normal deformation that may be determined by the stiffness of that membrane 645. The normal elasticity measurement of the tissue can be determined from relative deflection of the membranes 645 in the first and second sensors 600a-b. In such circumstances, the sensor signals from the electrode pairs at the first and second sensors 600a-b can be received by the control unit 80, which thereafter outputs of the display device 82 measurements of both Young's modulus and the shear modulus (or other tissue properties).

For example, as previously described, the control unit 80 can be equipped with a memory device having computer-readable instructions stored thereon that, when executed by a processor, cause the control system to implement an algorithm that computes the normal modulus of elasticity and the shear modulus of elasticity for the contacted tissue or material. In some embodiments, the algorithm that is executed by the processor of the control unit 80 uses averages or differences of capacitances among the multiple capacitors of each sensor 600a and 600b to determine the normal and shear components. For example, the normal component of the load upon the sensor 600a can be determined by averaging the displacement of the four electrodes 630a-d within the sensor 600a (e.g., measured by the change in capacitances as previously described). In another example, the shear component of the load upon the sensor 600a can be determined by measuring the differences in the displacement of the four electrodes 630a-d within the sensor 600a. Further, because the first sensor 600a has a more flexible membrane that the second sensor 600b, the ratios in displacements between these two sensors 600a-b can be used to calculate the elastic properties of the tissue or other material with which the sensor system is in contact. For example, the normal modulus of elasticity (e.g., the Young's modulus in this embodiment) can be calculated from the ratios of the normal components of the displacements of the membranes of the two sensors 600a-b. In another example, the shear modulus of elasticity can be calculated from the ratios of the shear components of the displacements of the membranes of the two sensors 600a-b. By using normal components for normal modulus of elasticity calculation, the sensor array will be able to measure both forces and elasticity accurately even when the contact between the sensor system and the tissue (or other contacted material) is oblique (e.g., not normal to the sensor surface).

Accordingly, the tissue elasticity sensor system (including the array of the sensors 600a-b) can provide accurate measurement of the tissue stiffness properties even when the probe or other medical instrument is in oblique contact with the targeted tissue (e.g., the targeted tissue is not necessarily arranged in a normal orientation relative to the sensor surface).

Figure 14A:
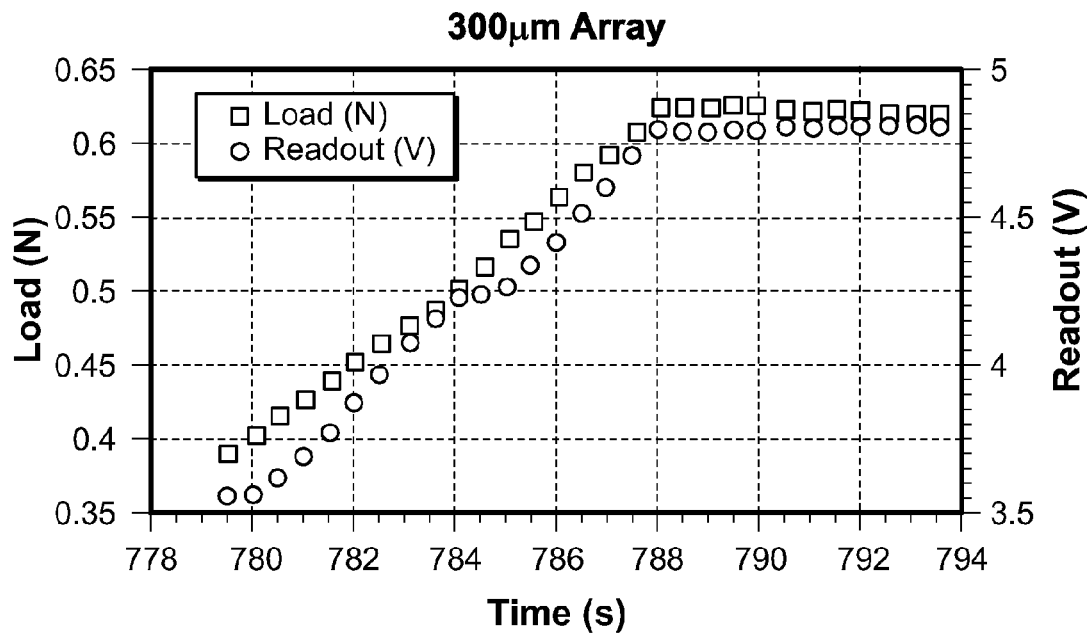
FIGS. 14A-C are plots of loads and capacitive readouts data for a sensor having 300 µm, 400 µm and 200 µm membrane sizes.
Figure 14B:
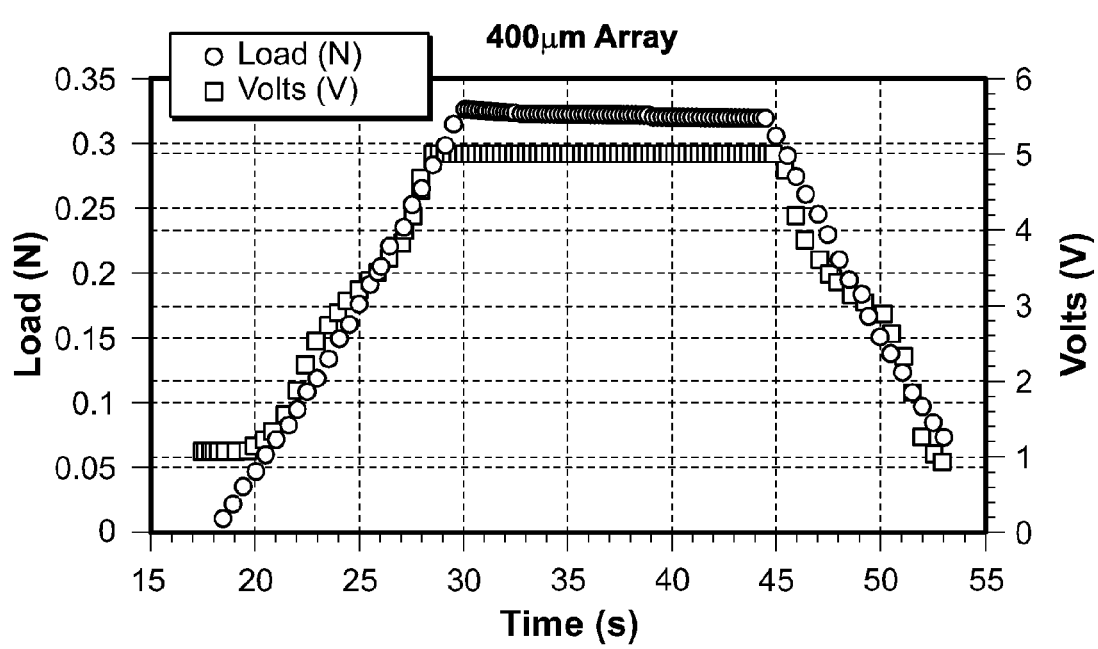
Figure 14C:
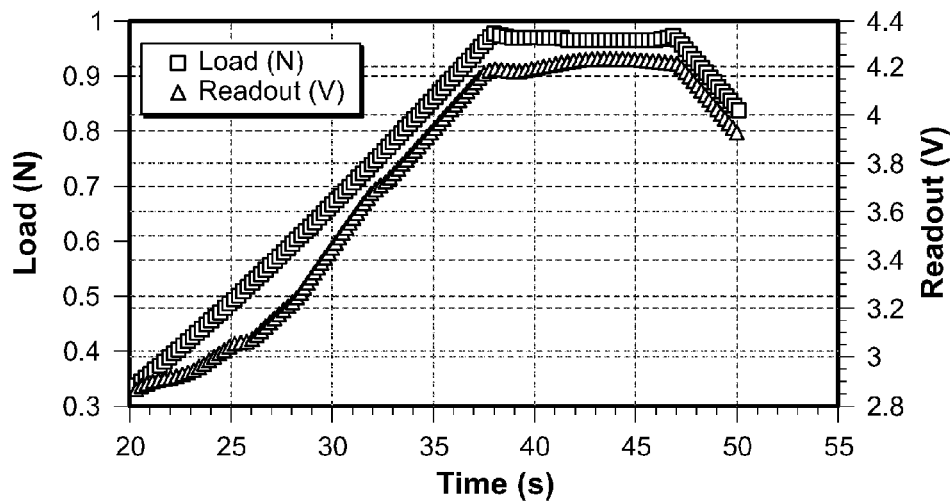

Referring now to FIGS. 14A-C, the tissue elasticity sensors described herein can be configured to provide a measurement of the force applied to the targeted tissue or other contact site. For example, for the tissue elasticity sensor 100 described in connection with FIGS. 1-6, the total capacitance measurement for all of the sensor membranes 120a-c of each sensor can be correlated to the total applied force on each sensor. For example, FIGS. 14A-C illustrate the variation of applied force and corresponding capacitive readout for three arrays of membranes having different diameters. The load applied on the sensor membrane arrays can be controlled for purposes of testing, for example, by applying a probe of a micro-mechanical tester and measured by a load cell that was embedded on the probe. The capacitive readout represents a single-channel readout from a capacitive measurement controller circuit 170 (FIG. 6). For a load range of about 0.35N to 0.55N, the change in voltage readings is around 1 V which corresponds to a capacitance change of about 1 pF. The controller circuit 170 can measure a capacitance change of about 0.001 pF. This can correspond to a membrane force measurement of about 0.2 mN. As shown in FIGS. 14A-C, the shapes of capacitive readout curves for the 400 µm, 300 µm and 200 µm membrane arrays resemble the shapes of the load curves for these membrane arrays. Accordingly, the displacement of membrane arrays for the sensor 100 can serve as a measure the applied force on the sensor 100 (e.g., when contacting against a targeted tissue site).

Figure 15A:
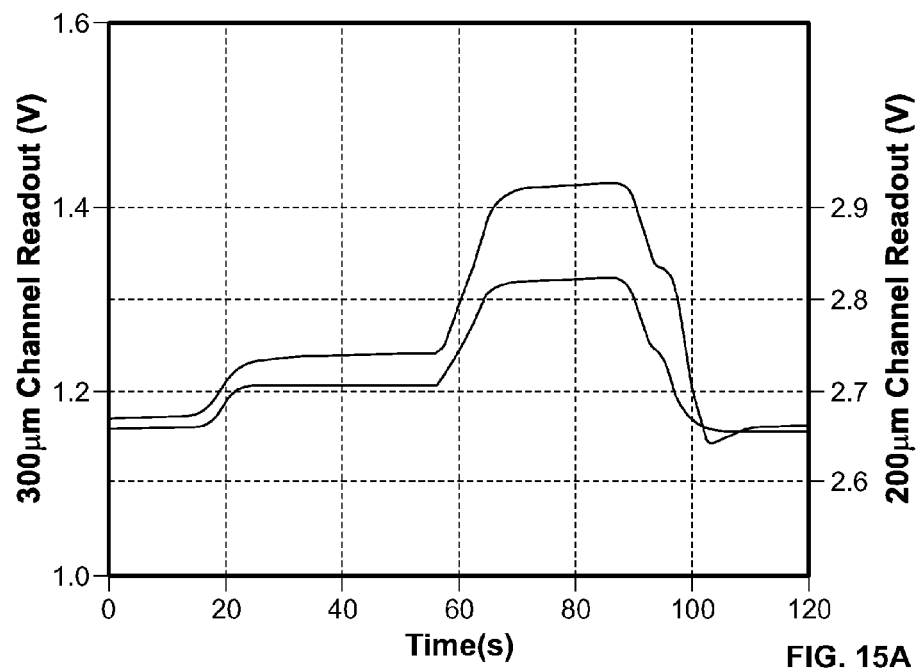
FIG. 15A is a plot of capacitive readout data for a sensor that approaches and contacts a target over time.
Figure 15B:
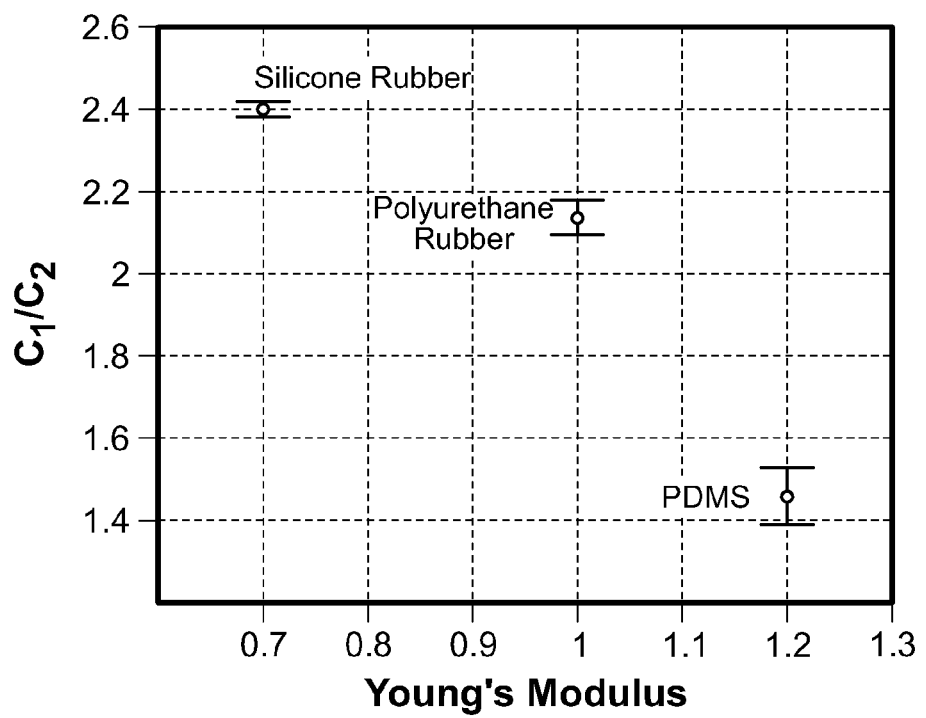
FIG. 15B is a plot of the variation of the ratio of capacitance changes of a tissue elasticity sensor with the elasticity modulus of known materials.

Referring now to FIGS. 15A-B, As previously described, the capacitance ($C_1$) measured at a first sensor membrane 120a (FIGS. 3-5C) can be compared to the capacitance ($C_2$) measured at a second sensor membrane 120b (FIGS. 3-5C) so as to determine a ratio of a first stress to a second stress ($\sigma_1$ and $\sigma_2$). Accordingly, the ratio of the two difference capacitances ($C_1/C_2$) can also be correlated to an estimated value of an elasticity modulus of a contacted material (where the sensor membranes are substantially smaller than the contact area of the targeted material). As shown in FIG. 15A, the simultaneous readouts from two channels connected to a stiffness sensor having two sensing membranes with different diameters were used to calculate the capacitive change of the two membranes. In this example, the sensor membranes approached the targeted material before time t=60 s and began to contact the targeted material at time t=60 s. In a series of experiments, the simultaneous two-channel readout was obtained by applying a series of square waves generated by a DAQ board (SCB-68 available from National Instruments, Austin, Tex.) to alternately activate the two capacitive readout chips (FIG. 6) that correspond to the two membranes at a frequency of 100 Hz. Different polymers (e.g., silicon rubber, polyurethane rubber and PDMS) with different thickness were used to touch the sensor 100. As shown in FIG. 15B, the ratio of capacitance changes of the two membranes can be correlated to the elasticity modulus of the probe material. Accordingly, the tissue elasticity sensors described herein can be used to estimate material elasticity characteristics such as Young's modulus. The correlation between the ($C_1/C_2$) value and the elasticity modulus value can be dependent upon several sensor calibration parameters, such as the sensor membrane material properties and dimensions. Once these calibration parameters have been obtained for a particular sensor design, the elasticity modulus can be calculated for a targeted tissue using these calibration parameters.

Figure 16:
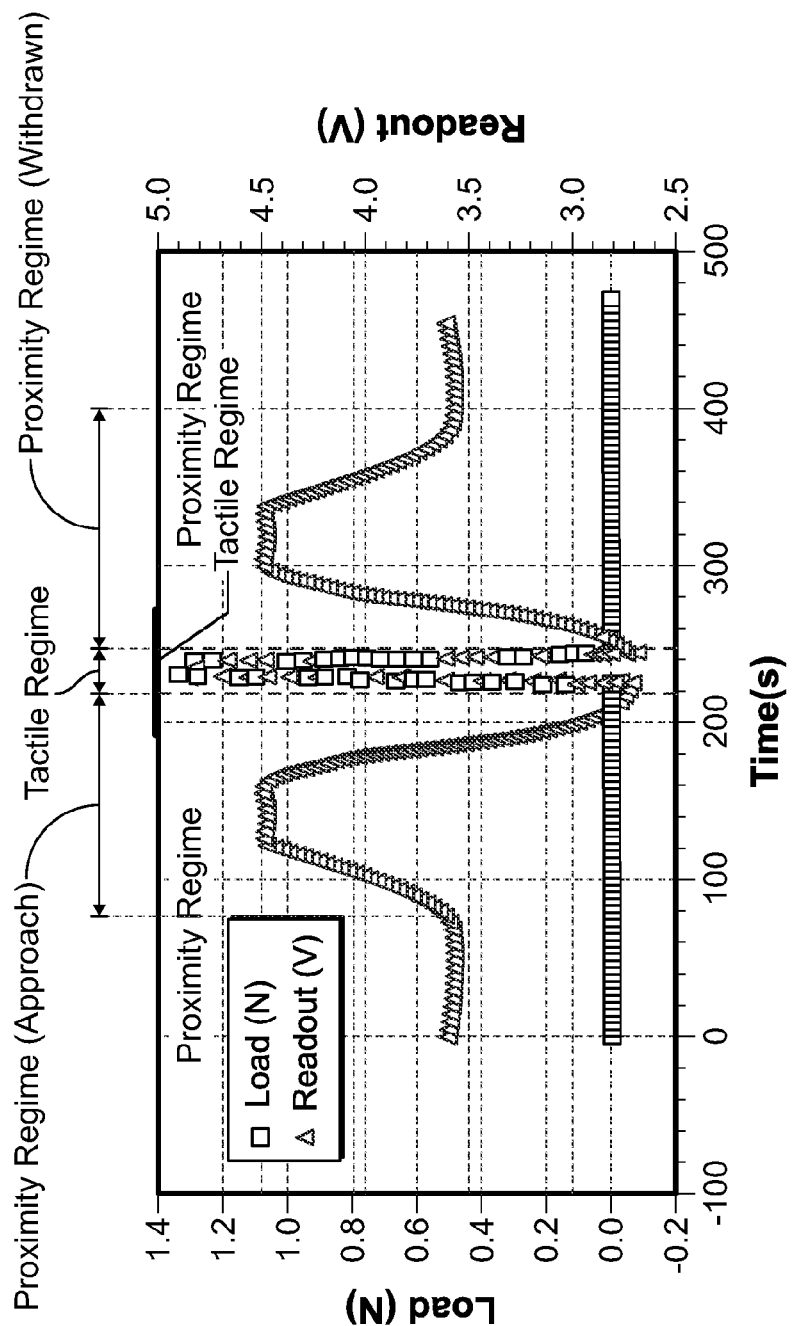
FIG. 16 is a plot of sensor data indicative of proximity sensing by a tissue elasticity sensor.

Referring now to FIG. 16, some embodiments of the tissue elasticity sensors 100, 300, and 600 can be used to sense proximity to a targeted surface, such as the targeted tissue site. For example, as the sensor 100 (FIGS. 3-4) approaches a targeted surface, the measured capacitance values slightly change even before the targeted material is contacted (before the membranes are displaced). It is believed that this effect is caused by the fringe capacitance of the sensor as the sensor approaches the targeted surface to contact. Accordingly, the tissue elasticity sensors described herein may also serve as a proximity sensor for a minimally invasive surgical instrument or other medical device.

As shown in the example in FIG. 16, the proximity effect can be detectable in the capacitive sensor readings as the sensor 100 (FIGS. 1-6) approached the targeted material surface at a distance of less than about 2 cm. The proximity sensing regime ended when sensor membranes 120a-c made contact with the targeted material surface and the tactile regime started. In this example, the sensor and the targeted material approached one another from an initial separation of 1.2 cm with an approach speed of 50 µm/sec. No load was applied during this process until the instant the probe made contact with the sensor. Inside the proximity sensing regime, the readout of the sensor 100 first increased as the sensor approached near to the targeted surface. The readout reached its peak when the sensor 100 and the targeted material were about 3.5 mm apart and then decreased sharply until the contact point. At the tactile sensing regime, the readout of the sensor 100 increased rapidly with increasing load. This effect was due to the displacement of the sensor membranes 120a-c. The sensor 100 and the targeted material surface were then separated at the same rate of 50 µm/sec and the corresponding readout was the mirror image of the approach. In some implementations, the capacitance between the top electrodes of adjacent sensing membranes may be utilized to provide the proximity sensing. Such sensing features can be useful for a minimally invasive surgical instrument or other medical device so that a surgeon can be alerted when the instrument is approaching another tissue surface.

Figure 17A:
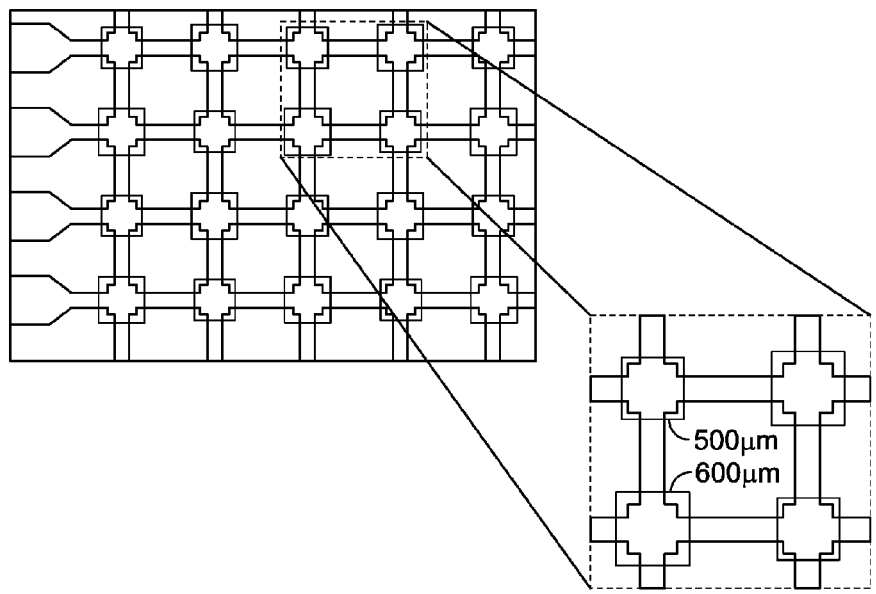
FIG. 17A is a top view of a micro-fabricated elasticity sensor array, in accordance with some embodiments.
Figure 17B:
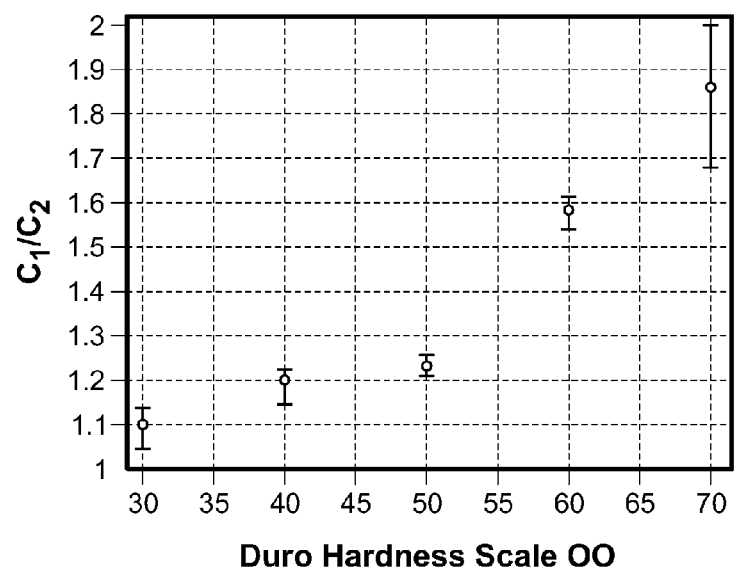
FIG. 17B is a plot of the variation of the ratio of capacitive changes of the sensor of FIG. 17A relative to the hardness of specimens in contact with the sensor.

Referring now to FIGS. 17A-B, an exemplary flexible sensor array 300 was micro-fabricated according to the process of FIG. 11 was examined for stiffness measurement. The flexible sensor array 300 included electroplated copper traces with a thickness of about 20 µm. The flexible sensor array 300 also included a 5×5 array of capacitor cells having two membrane sizes: 600 µm×600 µm and 500 µm×500 µm. In one experiment, sorbothane rubber specimens with various hardness from 30 Shore OO to 70 Shore OO were mounted on the flexible sensor array 300 surface. Predetermined loads were applied on the rubber specimens. The capacitances of the sensor capacitor cells were measured using a capacitance-to-digital converter (AD 7746 available from Analog Devices, Norwood, Mass.). As shown in FIG. 17B, as the Sorbothane rubber became stiffer, the difference of capacitive changes of capacitor cells with different membrane size became larger. Such experimental results can indicate that the flexible sensor array 300 can be configured to detect and differentiate targeted materials having varying stiffness characteristics. As previously described, such sensing features can be useful for a minimally invasive surgical instrument or other medical device so that information indicative of tissue type and tissue elasticity characteristics can be communicated in real-time to a surgeon or other user.

A number of embodiments of the invention have been described. Nevertheless, it will be understood that various modifications may be made without departing from the spirit and scope of the invention. Accordingly, other embodiments are within the scope of the following claims.

What is claimed is:

1. A medical system, comprising:
   a medical instrument having a distal portion insertable into a body and toward a targeted tissue;
   one or more tissue elasticity sensors coupled to the distal portion of the medical instrument, the one or more tissue elasticity sensors transmitting sensor signals in response to application of a force on the targeted tissue in the body that causes a displacement of the targeted tissue, wherein each of the tissue elasticity sensors includes two or more flexible membranes having different stiffness properties; and
   a control unit to determine both the Young's modulus of the targeted tissue and the shear modulus of the targeted tissue in the body in response to the sensor signals after the application of the force on the targeted tissue that causes the displacement of the targeted tissue.

2. The system of claim 1, wherein each of the two or more membranes of each tissue elasticity sensor maintains a capacitive gap between two electrodes.

3. The system of claim 2, wherein when each tissue elasticity sensor is pressed against the targeted tissue in the body, the two or more membranes having different stiffness properties are deflected by different amounts so that the capacitive gap is changed.

4. The system of claim 3, wherein the control unit detects capacitance changes to determine the relative displacement of the two or more membranes of each tissue elasticity sensor.

5. The system of claim 1, wherein the control unit determines both the Young's modulus of the targeted tissue and the shear modulus of the targeted tissue when the targeted tissue has oblique contact with an outer surface of the one or more tissue elasticity sensors coupled to the distal portion of the medical instrument.

6. The system of claim 1, wherein the control unit determines both the Young's modulus of the targeted tissue and the shear modulus of the targeted tissue in response to the sensor signals after the application of a non-predetermined force on the targeted material that causes a non-predetermined displacement of the targeted material.

7. The system of claim 1, wherein the medical instrument comprises at least one of a probe, an arthroscopic tool, an endoscopic tool, and a catheter.

8. A medical system, comprising:
   a medical instrument having a distal portion insertable into a body and toward a targeted tissue;
   one or more tissue elasticity sensors coupled to the distal portion of the medical instrument, the one or more tissue elasticity sensors transmitting sensor signals in response to application of a force on the targeted tissue in the body that causes a displacement of the targeted tissue, wherein the one or more tissue elasticity sensors coupled to the distal portion of the medical instrument comprise an array of micro-fabricated sensors including a first sensor having a first membrane adjacent to a first capacitive gap and a second sensor having a second membrane adjacent to a second capacitive gap, wherein the first membrane of the first sensor is different from the second membrane of the second sensor such that the first capacitive gap of the first sensor displaces differently from the second capacitive gap in response to any of a normal load and a shear load upon the array of micro-fabricated sensors; and
   a control unit to determine both the Young's modulus of the targeted tissue and the shear modulus of the targeted tissue in the body in response to the sensor signals after the application of the force on the targeted tissue that causes the displacement of the targeted tissue.

9. The system of claim 8, wherein the first membrane of the first sensor maintains four electrode adjacent to the first capacitive gap, and the second membrane of the second sensor maintains four electrode adjacent to the second capacitive gap.

10. The system of claim 9, wherein the control unit determines the Young's modulus of the targeted tissue and the shear modulus of the targeted tissue based at least in part on the ratio of a displacement of the first capacitive gap relative to a displacement of the second capacitive gap.

11. The system of claim 8, wherein the control unit determines both the Young's modulus of the targeted tissue and the shear modulus of the targeted tissue when the targeted tissue has oblique contact with an outer surface of the one or more tissue elasticity sensors coupled to the distal portion of the medical instrument.

12. The system of claim 8, wherein the control unit determines both the Young's modulus of the targeted tissue and the shear modulus of the targeted tissue in response to the sensor signals after the application of a non-predetermined force on the targeted material that causes a non-predetermined displacement of the targeted material.

13. The system of claim 8, wherein the medical instrument comprises at least one of a probe, an arthroscopic tool, an endoscopic tool, and a catheter.

14. A medical system, comprising:
   a medical instrument having a distal portion insertable into a body and toward a targeted tissue;
   one or more tissue elasticity sensors coupled to the distal portion of the medical instrument, the one or more tissue elasticity sensors transmitting sensor signals in response to application of a force on the targeted tissue in the body that causes a displacement of the targeted tissue; and
   a control unit to determine both the Young's modulus of the targeted tissue and the shear modulus of the targeted tissue in the body in response to the sensor signals after the application of the force on the targeted tissue that causes the displacement of the targeted tissue, wherein the distal portion of the medical instrument is equipped with an array of the tissue elasticity sensors so that a display device of the control unit, in response to receiving the sensor signals from the one or more tissue elasticity sensors, outputs a map of tissue elasticity measurements relative to positions along the distal portion of the medical instrument.

15. The system of claim 14, wherein the control unit determines both the Young's modulus of the targeted tissue and the shear modulus of the targeted tissue when the targeted tissue has oblique contact with an outer surface of the one or more tissue elasticity sensors coupled to the distal portion of the medical instrument.

16. The system of claim 14, wherein the control unit determines both the Young's modulus of the targeted tissue and the shear modulus of the targeted tissue in response to the sensor signals after the application of a non-predetermined force on the targeted material that causes a non-predetermined displacement of the targeted material.

17. The system of claim 14, wherein the medical instrument comprises at least one of a probe, an arthroscopic tool, an endoscopic tool, and a catheter.

18. A medical system, comprising:
a medical instrument having a distal portion insertable into a body and toward a targeted tissue;
one or more tissue elasticity sensors coupled to the distal portion of the medical instrument, the one or more tissue elasticity sensors transmitting sensor signals in response to application of a force on the targeted tissue in the body that causes a displacement of the targeted tissue; and
a control unit to determine both the Young's modulus of the targeted tissue and the shear modulus of the targeted tissue in the body in response to the sensor signals after the application of the force on the targeted tissue that causes the displacement of the targeted tissue, wherein the control unit comprises a display device that outputs information indicative of a type of tissue and a measurement indicative of a tissue elasticity characteristic in response to receiving the sensor signals from the one or more tissue elasticity sensors.

19. The system of claim 18, wherein the medical instrument comprises at least one of a probe, an arthroscopic tool, an endoscopic tool, and a catheter.

20. The system of claim 18, wherein the control unit determines both the Young's modulus of the targeted tissue and the shear modulus of the targeted tissue when the targeted tissue has oblique contact with an outer surface of the one or more tissue elasticity sensors coupled to the distal portion of the medical instrument.

21. The system of claim 18, wherein the control unit determines both the Young's modulus of the targeted tissue and the shear modulus of the targeted tissue in response to the sensor signals after the application of a non-predetermined force on the targeted material that causes a non-predetermined displacement of the targeted material.

22. A medical system, comprising:
a medical instrument having a distal portion deliverable toward a targeted material;
one or more material elasticity sensors coupled to the distal portion of the medical instrument, the one or more material elasticity sensors transmitting sensor signals in response to application of a non-predetermined force on the targeted material that causes a non-predetermined displacement of the targeted material, wherein each of the material elasticity sensors includes two or more flexible membranes having different stiffness properties, and each of the two flexible membranes maintains a capacitive gap between two electrodes; and
a control unit to determine a material elasticity modulus value of the targeted material in response to the sensor signals after the application of the non-predetermined force on the targeted material that causes the non-predetermined displacement of the targeted material.

23. The system of claim 22, wherein when each tissue elasticity sensor is pressed against the targeted tissue in the body, the two or more flexible membranes having different stiffness properties are deflected by different amounts so that the capacitive gap maintained by each flexible membrane is changed.

24. The system of claim 22, wherein the control unit determines both the Young's modulus of the targeted tissue and the shear modulus of the targeted tissue when the targeted tissue has oblique contact with an outer surface of the one or more material elasticity sensors coupled to the distal portion of the medical instrument.

25. The system of claim 22, wherein the control unit determines both the Young's modulus of the targeted tissue and the shear modulus of the targeted tissue in response to the sensor signals after the application of the non-predetermined force on the targeted material that causes the non-predetermined displacement of the targeted material.

26. The system of claim 22, wherein the medical instrument comprises at least one of a probe, an arthroscopic tool, an endoscopic tool, and a catheter.

27. A medical system, comprising:
a medical instrument having a distal portion deliverable toward a targeted material;
one or more material elasticity sensors coupled to the distal portion of the medical instrument, the one or more material elasticity sensors transmitting sensor signals in response to application of a non-predetermined force on the targeted material that causes a non-predetermined displacement of the targeted material, wherein the one or more material elasticity sensors comprise a micro-fabricated array of material elasticity sensors including a first sensor having a first membrane adjacent to a first capacitive gap and a second sensor having a second membrane adjacent to a second capacitive gap, wherein the first membrane of the first sensor is different from the second membrane of the second sensor such that the first capacitive gap of the first sensor displaces differently from the second capacitive gap in response to any of a normal load and a shear load upon the array of micro-fabricated sensors; and
a control unit to determine a material elasticity modulus value of the targeted material in response to the sensor signals after the application of the non-predetermined force on the targeted material that causes the non-predetermined displacement of the targeted material.

28. The system of claim 27, wherein the first membrane of the first sensor maintains at least four electrodes adjacent to the first capacitive gap, and wherein the second membrane of the second sensor maintains at least four electrodes adjacent to the second capacitive gap.

29. The system of claim 28, wherein the targeted material comprises a targeted tissue, wherein the distal portion of the medical instrument is insertable into a body and toward the targeted tissue.

30. The system of claim 29, wherein the one or more material elasticity sensor comprise tissue elasticity sensors for measuring elasticity characteristics of bodily tissue, and wherein the control unit determines a tissue elasticity modulus value a targeted tissue in response to the sensor signals.

31. The system of claim 27, wherein the control unit determines both the Young's modulus of the targeted tissue and the shear modulus of the targeted tissue when the targeted tissue has oblique contact with an outer surface of the one or more material elasticity sensors coupled to the distal portion of the medical instrument.

32. The system of claim 27, wherein the control unit determines both the Young's modulus of the targeted tissue and the shear modulus of the targeted tissue in response to the sensor signals after the application of the non-predetermined force on the targeted material that causes the non-predetermined displacement of the targeted material.

33. The system of claim 27, wherein the medical instrument comprises at least one of a probe, an arthroscopic tool, an endoscopic tool, and a catheter.

* * * * *

UNITED STATES PATENT AND TRADEMARK OFFICE
CERTIFICATE OF CORRECTION

PATENT NO. : 9,060,713 B2
APPLICATION NO. : 13/263411
DATED : June 23, 2015
INVENTOR(S) : Rajesh Rajamani et al.

It is certified that error appears in the above-identified patent and that said Letters Patent is hereby corrected as shown below:

In the specification,

Column 1, Lines 5-8, please delete "The invention described herein was made in part with funding under grant no. 0652208, from the National Science Foundation. The US government may have certain rights in the claimed subject matter." and insert -- This invention was made with government support under 0652208 awarded by the National Science Foundation. The government has certain rights in the invention. --, therefor.

Signed and Sealed this
Twenty-third Day of February, 2016

Michelle K. Lee
*Director of the United States Patent and Trademark Office*